US012605358B2

(12) United States Patent
Kim et al.

(10) Patent No.: US 12,605,358 B2
(45) Date of Patent: Apr. 21, 2026

(54) COMPOSITION FOR PREVENTING OR TREATING NERVOUS SYSTEM DISEASES COMPRISING COMPOUND THAT INHIBITS mTOR SIGNALING PATHWAY AS ACTIVE INGREDIENT

(71) Applicant: ALIAD BIOPHARMA, Yongin-si (KR)

(72) Inventors: Yunhee Kim, Seoul (KR); Hyockman Kwon, Seoul (KR); Young Taek Han, Cheonan-si (KR)

(73) Assignee: ALIAD BIOPHARMA, Yongin-si (KR)

( * ) Notice: Subject to any disclaimer, the term of this patent is extended or adjusted under 35 U.S.C. 154(b) by 365 days.

(21) Appl. No.: 18/277,701

(22) PCT Filed: Feb. 16, 2022

(86) PCT No.: PCT/KR2022/002261
§ 371 (c)(1),
(2) Date: Aug. 17, 2023

(87) PCT Pub. No.: WO2022/177280
PCT Pub. Date: Aug. 25, 2022

(65) Prior Publication Data

US 2024/0197673 A1 Jun. 20, 2024

(30) Foreign Application Priority Data

Feb. 17, 2021 (KR) ........................ 10-2021-0021201

(51) Int. Cl.
*A61K 31/357* (2006.01)
*A61K 9/00* (2006.01)
(Continued)

(52) U.S. Cl.
CPC .......... *A61K 31/357* (2013.01); *A61K 9/0019* (2013.01); *A61K 9/0043* (2013.01);
(Continued)

(58) Field of Classification Search
CPC .............................. A61K 31/357; A61P 25/28
See application file for complete search history.

(56) References Cited

FOREIGN PATENT DOCUMENTS

WO 2004/054505 A2 7/2004

OTHER PUBLICATIONS

Machine translation from Google CN10228456A (2011); Foshan University.*

(Continued)

*Primary Examiner* — Bethany P Barham
(74) *Attorney, Agent, or Firm* — Sughrue Mion, PLLC

(57) ABSTRACT

The present invention relates to a novel compound that inhibits the mTOR signaling pathway, a method for preparing same, and a pharmaceutical composition comprising same as an active ingredient. The compound of the present invention was found to inhibit mTORC1 and mTORC2 activities, activate autophagy, and alleviate a series of disease symptoms associated with Alzheimer's-type dementia in dementia model animals, and thus can be effectively used as a pharmaceutical composition capable of preventing or treating nervous system diseases comprising neurodegenerative diseases and mTORopathy.

9 Claims, 17 Drawing Sheets

(51) Int. Cl.

| | |
|---|---|
| ***A61K 9/14*** | (2006.01) |
| ***A61K 9/20*** | (2006.01) |
| ***A61K 9/48*** | (2006.01) |
| ***A61K 47/02*** | (2006.01) |
| ***A61K 47/12*** | (2006.01) |
| ***A61K 47/14*** | (2017.01) |
| ***A61K 47/26*** | (2006.01) |
| ***A61P 25/28*** | (2006.01) |

(52) U.S. Cl.

CPC ............ *A61K 9/145* (2013.01); *A61K 9/2013* (2013.01); *A61K 9/2018* (2013.01); *A61K 9/2059* (2013.01); *A61K 9/4858* (2013.01); *A61K 9/4866* (2013.01); *A61K 47/02* (2013.01); *A61K 47/12* (2013.01); *A61K 47/14* (2013.01); *A61K 47/26* (2013.01); *A61P 25/28* (2018.01)

(56) References Cited

OTHER PUBLICATIONS

W. Bonthrone et al., "The Methylenation of Catechols", J. Chem. Soc. (C), 1969, pp. 1202-1204 (3 pages total).

Wertz, S. et al., "Cross dehydrogenative coupling via base-promoted homolytic aromatic substitution (BHAS): Synthesis of fluorenones and xanthones", Organic letters, 2013, pp. 928-931 and S1-S81 for supporting information, vol. 15, No. 4.

Xue, W. et al., "Discovery of potent PTP1B inhibitors via structure-based drug design, synthesis and in vitro bioassay of Norathyriol derivatives", Bioorganic chemistry, 2019, pp. 224-234, vol. 86.

Wang, S. - F et al., "Efficient aryl migration from an aryl ether to a carboxylic acid group to form an ester by visible-light photoredox catalysis", Angewandte Chemie, 2017, pp. 13997-14001 and S1-S127 for supporting information, vol. 129.

Hen, R. et al., "Synthesis and biological evaluation of disubstituted amidoxanthones as potential telomeric G-quadruplex DNA-binding and apoptosis-inducing agents", Bioorganic & Medicinal Chemistry, 2016, pp. 619-626, vol. 24.

Ghosal, S. et al., "Regioselective cleavage of methylenedioxy ring in xanthones: an entry into immuno-stimulant 7-glucosyloxypolymethoxyxanthones", Chemischer Informationsdienst, 1985, 2 pages, vol. 16, No. 21.

Chemical abstract compounds, STNext. RN 14103-15-2 (Nov. 16, 1984) and RN 14103-14-1 (Nov. 16, 1984), 1 page.

International Search Report of PCT/KR2022/002261 dated Jun. 2, 2022 [PCT/ISA/210].

* cited by examiner

COMPOSITION FOR PREVENTING OR TREATING NERVOUS SYSTEM DISEASES COMPRISING COMPOUND THAT INHIBITS mTOR SIGNALING PATHWAY AS ACTIVE INGREDIENT

CROSS REFERENCE TO RELATED APPLICATIONS

This application is a National Stage of International Application No. PCT/KR2022/002261 filed on Feb. 16, 2022, claiming priority based on Korean Patent Application No. 10-2021-0021201 filed on Feb. 17, 2021, the entire disclosures of which are incorporated herein by reference.

TECHNICAL FIELD

The present invention relates to a novel compound that inhibits an mTOR signaling pathway, a method for preparing the same, and a pharmaceutical composition including the same as an active ingredient.

BACKGROUND ART

Alzheimer's disease, a representative neurodegenerative disease, is a progressive brain disease caused by a gradual decrease in brain neurons, and senile plaques caused by Aβ accumulated around neurons and neurofibrillary tangles (NFTs) accumulated by entanglement caused by hyperphosphorylation of tau inside neurons are observed as major abnormal lesions.

The Aβ is produced by cleavage of APP by β- and γ-secretase due to mutations occurring in amyloid precursor protein (APP), presenilin-I (PS-I), or presenilin-II (PS-II), but is not removed but accumulated due to an abnormal structure (β), and mutations in APP, PS-I, PS-II, tau, etc. are genetic factors for the onset of Familial Alzheimer's disease (FAD). Both the senile plaques and NFTs are generated and accumulated by abnormal protein homeostasis, and induce the death of surrounding neurons, and Aβ oligomers and hyperphosphorylated tau oligomers are transferred to neighboring neurons through synapses to gradually kill more cells.

So far, a therapeutic agent for Alzheimer's disease has been not developed that treats the cause of the disease other than drugs that alleviate symptoms. As drugs to remove the senile plaques, at least 100 candidate drugs, including β-secretase inhibitors, γ-secretase inhibitors, and monoclonal antibodies that recognize Aβ to help to disintegrate senile plaques, have entered clinical trials, but almost all failures were declared and discontinued in 2018 and 2019, as clinical results showed that a cognitive function was not restored even if candidate drugs removed the senile plaques. The Food and Drug Administration (FDA) granted accelerated approval for aducanumab (Biogen), a monoclonal antibody that binds to Aβ aggregates and induces disintegration of senile plaques, as a therapeutic agent for early Alzheimer's disease in 2021, but controversy over treatment efficacy has continued. As a currently used dementia therapeutic agent, an acetylcholinesterase inhibitor (Ach esterase inhibitor), which delays a decrease in mental function, rather than drugs that treat the cause of the disease, has been used as a major drug.

A mammalian target of rapamycin (mTOR) complex serves to regulate intracellular protein synthesis and autophagy and cause cell growth. Specifically, the mTOR is serine/threonine kinase, and acts as a center of a signaling hub that combines internal and external signals in cells and regulates cell metabolism, growth, proliferation, and survival. Accordingly, abnormalities in mTOR signaling are found in many diseases, and mTOR excessive signaling is particularly problematic in nervous system diseases, cancer, etc. (Lipton & Sahin (2014) Neuron 84: 275-291).

For example, it has been found that an increase in the mTOR signal or the phosphorylation of S6K, a downstream signal transducer of mammalian Target of rapamycin complex 1 (mTORC1), increases in proportion to the accumulation of Aβ and NFT in brain tissue of patients with Alzheimer's disease, and the pathological accumulation of hyperphosphorylated tau is related to activation of mTOR protein according to S2481 phosphorylation (Li et al. (2005) FEBS J. 272: 4211-4220). In addition, AKT, which activates mTORC1, is increased in the temporal lobe of patients with Alzheimer's disease, and inhibition of the mTOR signal shows physiological and behavioral relief in an animal model that accumulates Aβ. A decrease in the amount of Aβ by drugs or genetic manipulation is accompanied by a decrease in the activity of an mTOR pathway, and even in Parkinson's disease (PD) and Huntington's disease (HD), which are types of neurodegenerative diseases, it was found that the inhibition of the mTOR pathway alleviates disease symptoms (Lipton & Sahin (2014) Neuron 84: 275-291).

On the other hand, the mTOR complex is present as mTORC1, which consists of mTOR, mLST8, DEPTOR, Tti1/Tel2, RAPTOR, and PRAS40 as constituent proteins, and mammalian target of rapamycin complex 2 (mTORC2), which consists of mTOR, mLST8, DEPTOR, Tti1/Tel2, RICTOR, mSIN1, and PROTOR1/2 as constituent proteins, and both are proposed to be associated with brain diseases, autism, etc., but the two complexes have different functions (Saxton & Sabatini (2017) Cell 168: 960-976). For example, the mTORC1 detects intracellular nutrients and energy levels and triggers anabolism only when there is room. For example, eukaryotic translation initiation factor 4E-binding protein 1 (4E-BP1) is phosphorylated to activate cap-dependent mRNA translation and promote de novo fat synthesis. On the other hand, the mTORC2 serves to induce cell survival and proliferation according to external signals and interact at an appropriate time and place. For example, the mTORC2 is activated in response to PI3K stimulation by growth factors such as insulin, and phosphorylates AGC kinases such as AKT, SGK, and PKC to redistribute the actin cytoskeleton and promote the cell survival and proliferation. In addition, neuroplasticity such as metabotropic glutamate receptor-mediated long-term depression (mGluR-LTD) is also regulated by mTORC2.

In a neurogenesis process, the mTOR signal of neural progenitor cells is a major regulator of maintenance of stemness and differentiation of neurons and glia. An increased mTOR signal by mutations in phosphatase and tensin homolog (PTEN) or tuberous sclerosis 1/2 (TSC1/2), which is a gene regulating the mTORC1 pathway at upstream, has a great effect on neural structure and differentiation (Lipton & Sahin (2014) Neuron 84: 275-291). In TSC1/2-deleted neurons, the number of axons increases, and in hippocampal neurons, the soma increases and a size in dendritic arbor increases, but the number of dendritic spines decreases (Tavazoie et al. (2005) Nat. Neurosci. 8: 1727-1734). Even in a Tsc1-deleted animal model, large neurons and less plastic neurons and glia are also found (Uhlmann et al. (2002) Ann. Neurol. 52: 285-296).

The functional division of mTORC1 and mTORC2 described above has been reported in developing raptor and rictor knockout (KO) mice. Brain-specific raptor KO transgenic mice shows microcephaly, decreased neuronal cell size, apoptosis, and high mortality in early life (Cloetta et al. (2013) J. Neurosci. 33: 7799-7810). In addition, in oligodendrocytes of the spinal cord, mTORC1 promotes the initiation and thickness of myelination.

In rictor KO mice of mTORC2, a decreased dendrite length is shown in addition to microcephaly and decreased neuronal soma size (Thomanetz et al. (2013) J. Cell Biol. 201: 293-308), but there is no change in phosphorylation of S6K1 and 4EBP1, and thus this seems to be a phenomenon irrelevant to mTORC2. The mTORC2 activates Rho and Rac to organize the cytoskeleton and acts on synapse formation and function, but when the Rho and Rae are activated too much, the number of dendritic spines is increased, but the dendritic spines are not matured.

When rapamycin, a representative inhibitor of mTOR, is administered to a dementia model animal for a long time, loss of memory and cognitive functions associated with dementia is restored, and not only Aβ is reduced, but also autophagy is increased, thereby delaying or suppressing the progression of dementia disease symptoms (Spilman et al. (2010) PLoS One 4: e9979). However, since the rapamycin has an immunosuppressive function and has severe side effects, the rapamycin is not used as a dementia therapeutic agent that requires long-term administration. The rapamycin inhibits mTORC1, but also inhibits mTORC2 when administered for a long time (Sarbassov et al. (2006) Mol. Cell 22: 159-168). Accordingly, it is unclear whether the dementia therapeutic effect of rapamycin on dementia is induced by mTORC1 inhibition or mTORC2 inhibition.

Activity-regulated cytoskeleton-associated protein (Arc) is one of immediate early genes of which expression is rapidly induced by synaptic activation, and Arc mRNA is rapidly transported and located to dendritic spines, which have been recently activated, in a translation-suppressed state. Thereafter, when the synapse where the Arc mRNA is located is activated at a relatively low frequency (<10 Hz) by synaptic activation, an activation signal of mGluR1/5 is transmitted and the Arc mRNA is translated, and the generated Arc protein promotes the endocytosis of α-Amino-3-hydroxy-5-methyl-4-isoxazolepropionic acid (AMPA) receptors to cause long term depression (LTD) that reduces synaptic activity (Wilkerson et al. (2018) Semin. Cell Dev. Biol. 77: 51-62). The mGluR-dependent LTD occurring in the hippocampus contributes to synaptic plasticity and plays a key role in new memory formation and cognitive functions.

When the APP is sequentially cleaved by α-secretase and γ-secretase, sAPPα, P3, and AICD50 are produced, and Aβ, which promotes the death of neurons, is not generated. On the other hand, when the APP is sequentially cleaved by β-secretase and γ-secretase, Aβ is generated with sAPPβ and AICD50. In addition, a nonamyloidogenic pathway in which Aβ is not generated from APP occurs in the cell membrane, whereas an amyloidogenic pathway in which Aβ is generated occurs in the endosome rather than the cell membrane (Rajendran & Annaert (2012) Traffic 13: 759-770). The Arc protein recruits γ-secretase into endosomes where APP and β-secretase are located to promote Aβ production through the amyloidogenic process of APP (Wu et al. (2011) Cell 147: 615-628). Thus, the Arc protein is a key regulator determining activity-dependent Aβ generation, which increases as neurons activate. Recently, it was found that mTORC2 is required to generate LTD in the hippocampus by mGluR signaling to synthesize the Arc protein (Zhu et al. (2018) Nat. Neurosci. 21: 799-802). The Aβ oligomer also activates the mTOR signaling pathway and increases Arc protein production (Caccamo et al. (2011) J. Biol. Chem. 286: 8924-8932; Lancor et al. (2004) J. Neurosci. 24: 10191-10200), and the signaling by the Aβ oligomer is mediated by $PrP^{c}$ and mGluR5 (Um et al. (2013) Neuron 79: 887-902). When considering that mGluR-dependent LTD formation is mediated by the internalization of endosomes containing an AMPA receptor by the Arc protein, the activity-dependent generation process of Aβ is also predicted to require mTORC2. Therefore, mTORC2 becomes a target protein for developing a therapeutic agent for Alzheimer's disease that inhibits Aβ generation.

In neurodegenerative diseases, proteins accumulated and produced by abnormal protein homeostasis, such as Aβ and tau-entangled NFT in Alzheimer's disease, huntingtin in Huntington's disease, synuclein in Parkinson's disease, and the like, are removed by autophagy. Autophagy or autophagocytosis is a regulatory mechanism by which cells self-degrade unnecessary or nonfunctional cellular components, and plays an important role in maintaining proteostasis by removing condensation or entanglement of cytotoxic proteins, damaged organelles, etc. (Levine et al. (2011) Nature 469: 323-335).

In the macroautophagy, a type of autophagy, double-membrane autophagosomes are formed, and abnormal proteins and damaged organelles are introduced, fused with lysosomes to form autolysosomes, and the contents thereof are degraded by hydrolase. The formation of double-membrane autophagosomes is promoted by Unc-51-like kinases, and mammalian homologues of Atg1 (ULK1 and ULK2), which are one of autophagy-related (ATG) proteins.

In mammals, when amino acid levels are increased or growth factor signals are detected, mTORC1 is activated, and mTORC1 phosphorylates ULK1 and ULK2 to inhibit autophagy (Kim et al. (2011) Nature Cell Biol. 13: 132-141). ULK phosphorylates and activates mammalian homologue of Atg6 (Beclin-1), and a ULK/Beclin-1 complex moves to phagophores, where autophagosomes are generated, to activate autophagy.

Rapamycin and its derivative, rapalog, inhibit mTORC1 activity to be highly anticipated as an autophagy promoter, but specifically, phosphorylation of ULK1 Ser758 and TFEB Ser142, which are mTORC1 substrates involved in autophagy, is not inhibited efficiently (Choo et al. (2008) Proc. Natl. Acad. Sci. USA 105: 17414-17419). Therefore, in order to use an mTORC1 inhibitor for promoting autophagy, the development of a new mTORC1 inhibitor having an inhibitory mechanism different from that of rapamycin has been required.

In the autophagy, a ubiquitin-like complex covalently attaches a lipid phosphatidylethanolamine (PE) on the surface of the autophagosome to an LC3 protein which is a mammalian homolog of a ubiquitin-like yeast protein ATG8 (Dooley et al. (2014) Mol. Cell 55: 238-252). Lipidized LC3 closes the autophagosome, so that cargo binds to p62, and the completed autophagosomes fuse with lysosomes. LC3 is referred to as LC3-I, and a PE-conjugated form of LC3 is referred to as LC3-II.

An mTORopathy is a genetic disease in which nervous system abnormalities are caused by somatic mutations of genes in the mTOR signaling pathway in germ cells or neurons (Karalis & Bateup (2021) Dev. Neurosci. 43: 143-158). The mTORopathy includes epilepsy, autism spectrum disorder, tuberous sclerosis (TSC), fragile X syndrome, and the like, and excessive activation of mTOR signaling mainly causes the mTORopathy. Mutations in a phosphatase and tensin homolog (PTEN) gene, which is an inhibitor of PI3K/mTOR signal, are typical examples of mTORopathy, and hyperactivation of mTOR signals cause macrocephaly, autism, epilepsy, mental retardation, etc. (Nguyen et al. (2015) Epilepsia 56: 636-646).

In the present invention, it was found that O-alkylated norathyriol derivatives inhibit the activities of mTORC1 and mTORC2 and induce autophagy, and it was found that a series of disease symptoms associated with Alzheimer's disease are alleviated in a dementia model animal, and a low-molecular compound effective for preventing or treating nervous system diseases including Alzheimer's disease, neurodegenerative diseases and mTORopathy has been synthesized.

DISCLOSURE

Technical Problem

The present inventors have made many efforts to find a novel compound capable of inhibiting activities of mTORC1 and mTORC2 and exhibiting preventive or therapeutic effects on nervous system diseases by inducing autophagy excellently, and as a result, found that a low-molecular-weight compound derived from a natural substance represented by Chemical Formula A in the present specification inhibited an mTOR pathway, induced autophagy to have excellent activity of removing Aβ accumulated in primary cultured brain neurons, restoring memory and cognitive dysfunction, which is a dementia-associated disease symptom in a dementia model animal, having excellent activity of alleviating senile plaques, NFT accumulation, and brain inflammatory responses, and promoting neurogenesis by differentiation of neural progenitor cells, thereby exhibiting a preventive or therapeutic effect on nervous system diseases, and then completed the present invention.

Therefore, an object of the present invention is to provide a compound represented by Chemical Formula A below or a pharmaceutically acceptable salt thereof:

[Chemical Formula A]

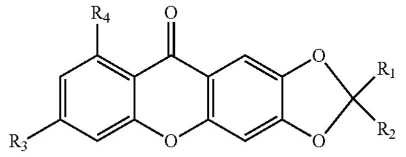

(in which, $R_1$ and $R_2$ are each a substituent selected from the group consisting of hydrogen, hydroxy, halogen, $C_1$ to $C_{10}$ straight-chain or branched alkyl, and $C_1$ to $C_{10}$ straight-chain or branched alkoxy, and $R_3$ and $R_4$ are each a substituent selected from the group consisting of hydrogen, hydroxy, halogen, $C_1$ to $C_{10}$ straight-chain or branched alkyl, $C_1$ to $C_{10}$ straight-chain or branched alkoxy, pyridinyl methoxy and benzyl oxy.).

Another object of the present invention is to provide a pharmaceutical composition for preventing or treating neurodegenerative diseases, including the compound or the pharmaceutically acceptable salt thereof as an active ingredient.

Another object of the present invention is to provide a pharmaceutical composition for preventing or treating mTORopathy, including the compound or the pharmaceutically acceptable salt thereof as an active ingredient.

Another object of the present invention is to provide a pharmaceutical composition for preventing or treating nervous system diseases by promoting neurogenesis, including the compound or the pharmaceutically acceptable salt thereof as an active ingredient.

Another object of the present invention is to provide a method for preparing a compound represented by Chemical Formula A2 below, including reacting norathyriol represented by Chemical Formula 1 below and a compound represented by Chemical Formula B1 below in the presence of an organic solvent and a base catalyst (step 1), as shown in Reaction Scheme 1 below:

[Reaction Scheme 1]

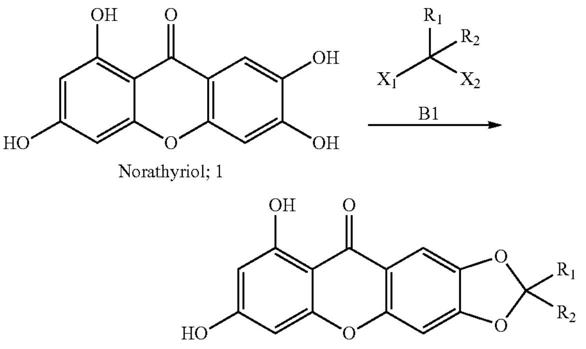

Norathyriol; 1

A2

(in which, $X_1$ and $X_2$ are each one of chloro, bromo, iodo, tosylate and mesylate, and $R_1$ and $R_2$ are each a substituent selected from the group consisting of hydrogen, hydroxy, halogen, $C_1$ to $C_{10}$ straight-chain or branched alkyl, and $C_1$ to $C_{10}$ straight-chain or branched alkoxy.).

Another object of the present invention is to provide a method for preparing a compound represented by Chemical Formula A3 below, including reacting a compound represented by Chemical Formula A2 below and a compound represented by Chemical Formula B2 below in the presence of an organic solvent and a base catalyst (step 1), as shown in Reaction Scheme 2 below:

[Reaction Scheme 2]

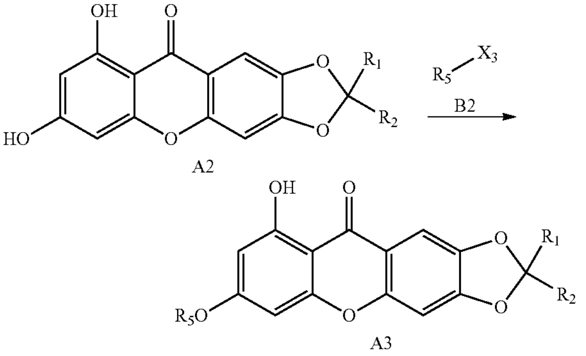

A2

A3

(in which, $X_3$ is each one of chloro, bromo, iodo, tosylate and mesylate, $R_1$ and $R_2$ are each a substituent selected from the group consisting of hydrogen, hydroxy, halogen, $C_1$ to $C_{10}$ straight-chain or branched alkyl, and $C_1$ to $C_{10}$ straight-chain or branched alkoxy, and $R_5$ is a substituent selected from the group consisting of hydrogen, $C_1$ to $C_{10}$ straight-chain or branched alkyl, pyridinyl and benzyl groups.).

Another object of the present invention is to provide a method for preparing a compound represented by Chemical Formula A4 below, including reacting a compound represented by Chemical Formula A2 below and a compound represented by Chemical Formula B3 below in the presence of an organic solvent and a base catalyst (step 1), as shown in Reaction Scheme 3 below:

[Reaction Scheme 3]

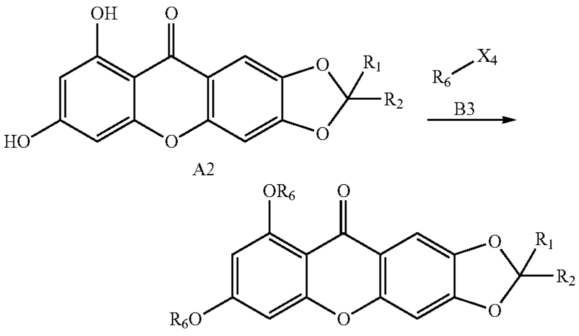

A2

A4

(in which, $X_4$ is each one of chloro, bromo, iodo, tosylate and mesylate, $R_1$ and $R_2$ are each a substituent selected from the group consisting of hydrogen, hydroxy, halogen, $C_1$ to $C_{10}$ straight-chain or branched alkyl, and $C_1$ to $C_{10}$ straight-chain or branched alkoxy, and $R_6$ is a substituent selected from the group consisting of hydrogen, $C_1$ to $C_{10}$ straight-chain or branched alkyl, pyridinyl and benzyl groups.).

Another object of the present invention is to provide a method for preparing a compound represented by Chemical Formula A6 below, including reacting a compound represented by Chemical Formula A3 below and a compound represented by Chemical Formula B4 below in the presence of an organic solvent and a base catalyst (step 1), as shown in Reaction Scheme 4 below:

[Reaction Scheme 4]

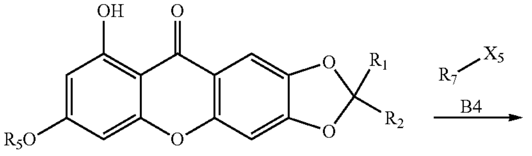

A3

-continued

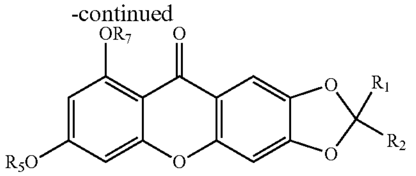
A6

(in which, $X_5$ is each one of chloro, bromo, iodo, tosylate and mesylate, $R_1$ and $R_2$ are each a substituent selected from the group consisting of hydrogen, hydroxy, halogen, $C_1$ to $C_{10}$ straight-chain or branched alkyl, and $C_1$ to $C_{10}$ straight-chain or branched alkoxy, and $R_5$ and $R_7$ are each a substituent selected from the group consisting of hydrogen, $C_1$ to $C_{10}$ straight-chain or branched alkyl, pyridinyl and benzyl groups.).

Another object of the present invention is to provide a method for preparing a compound represented by Chemical Formula A7 below, including reacting a compound represented by Chemical Formula A6 below and hydrogen gas in the presence of an organic solvent and a Pd/C catalyst (step 1), as shown in Reaction Scheme 5 below:

[Reaction Scheme 5]

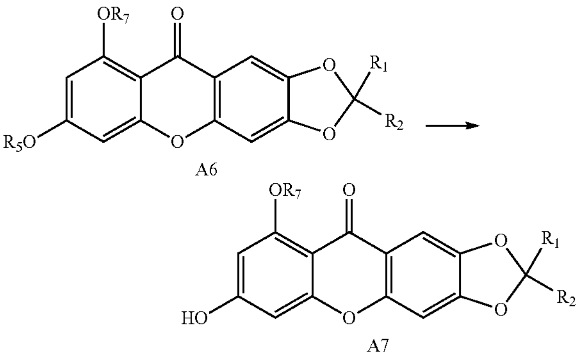
A6

A7

(in which, $R_1$ and $R_2$ are each a substituent selected from the group consisting of hydrogen, hydroxy, halogen, $C_1$ to $C_{10}$ straight-chain or branched alkyl, and $C_1$ to $C_{10}$ straight-chain or branched alkoxy, and $R_5$ and $R_7$ are each a substituent selected from the group consisting of hydrogen, $C_1$ to $C_{10}$ straight-chain or branched alkyl, pyridinyl and benzyl groups.).

Another object of the present invention is to provide a method for preparing a compound represented by Chemical Formula A20 below, as shown in Reaction Scheme 6 below, including:

synthesizing a compound represented by Chemical Formula A18-1 below by reacting a compound represented by Chemical Formula A18 below and a compound represented by Chemical Formula B5 below in the presence of an organic solvent and a base catalyst (step 1);

synthesizing a compound represented by Chemical Formula A18-2 below by reacting a compound represented by Chemical Formula A18-1 below and a phosphate in the presence of an organic solvent (step 2); and reacting a compound represented by Chemical Formula A18-2 below and phosphorus oxychloride ($POCl_3$) in the presence of an organic solvent (step 3):

[Reaction Scheme 6]

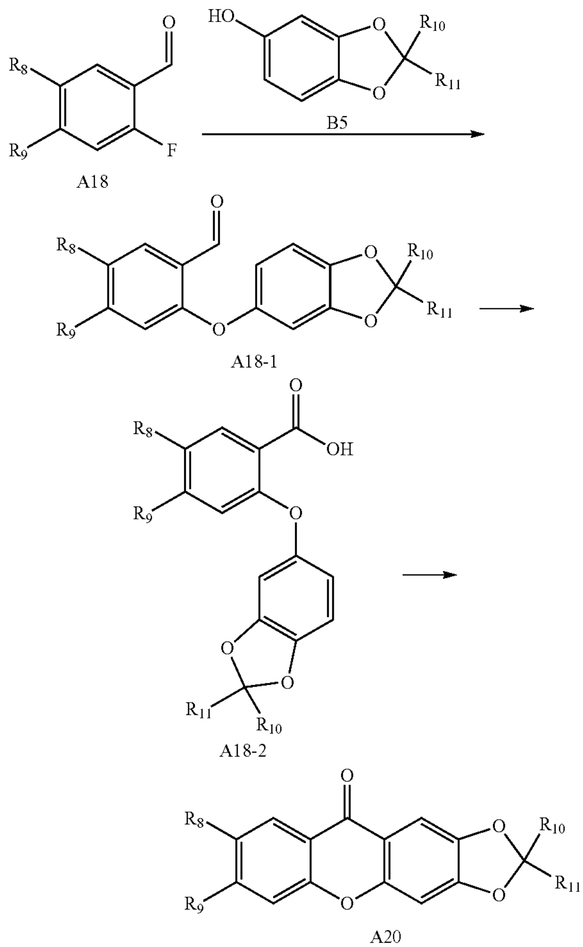

A18
A18-1
A18-2
A20

(in which, $R_8$, $R_9$, $R_{10}$ and $R_{11}$ are each a substituent selected from the group consisting of hydrogen, hydroxy, halogen, $C_1$ to $C_{10}$ straight-chain or branched alkyl, and $C_1$ to $C_{10}$ straight-chain or branched alkoxy.).

Technical Solution

In order to achieve the object, an aspect of the present invention provides a compound represented by Chemical Formula A below or a pharmaceutically acceptable salt thereof:

[Chemical Formula A]

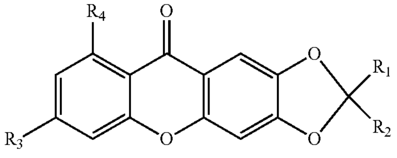

(in which, $R_1$ and $R_2$ are each a substituent selected from the group consisting of hydrogen, hydroxy, halogen, $C_1$ to $C_{10}$ straight-chain or branched alkyl, and $C_1$ to $C_{10}$ straight-chain or branched alkoxy, and $R_3$ and $R_4$ are each a substituent selected from the group consisting of hydrogen, hydroxy, halogen, $C_1$ to $C_{10}$ straight-chain or branched alkyl, $C_1$ to $C_{10}$ straight-chain or branched alkoxy, pyridinyl methoxy and benzyl oxy.).

Another aspect of the present invention provides a pharmaceutical composition for preventing or treating neurodegenerative diseases, including the compound or the pharmaceutically acceptable salt thereof as an active ingredient.

Yet another aspect of the present invention provides a pharmaceutical composition for preventing or treating mTORopathy, including the compound or the pharmaceutically acceptable salt thereof as an active ingredient.

Still another aspect of the present invention provides a pharmaceutical composition for preventing or treating nervous system diseases by promoting neurogenesis, including the compound or the pharmaceutically acceptable salt thereof as an active ingredient.

Still yet another aspect of the present invention provides a method for preparing a compound represented by Chemical Formula A2 below, including reacting norathyriol represented by Chemical Formula 1 below and a compound represented by Chemical Formula B1 below in the presence of an organic solvent and a base catalyst (step 1), as shown in Reaction Scheme 1 below:

[Reaction Scheme 1]

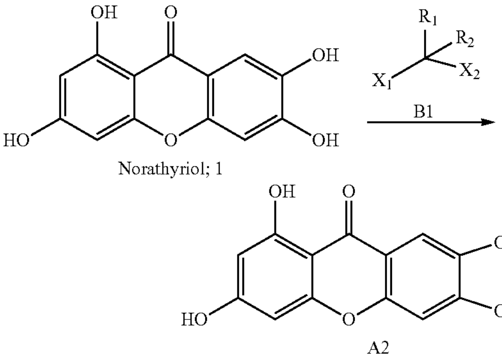

Norathyriol; 1
A2

(in which, $X_1$ and $X_2$ are each one of chloro, bromo, iodo, tosylate and mesylate, and $R_1$ and $R_2$ are each a substituent selected from the group consisting of hydrogen, hydroxy, halogen, $C_1$ to $C_{10}$ straight-chain or branched alkyl, and $C_1$ to $C_{10}$ straight-chain or branched alkoxy.).

Still yet another aspect of the present invention provides a method for preparing a compound represented by Chemical Formula A3 below, including reacting a compound represented by Chemical Formula A2 below and a compound represented by Chemical Formula B2 below in the presence of an organic solvent and a base catalyst (step 1), as shown in Reaction Scheme 2 below:

[Reaction Scheme 2]

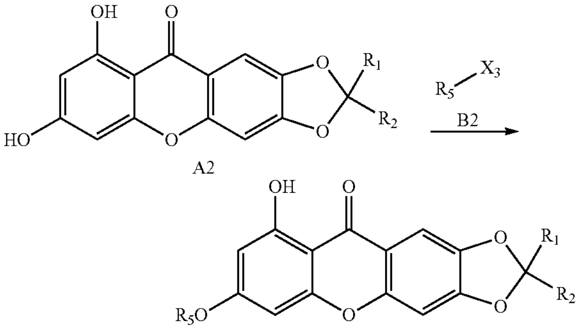

A2

A3

(in which, $X_3$ is each one of chloro, bromo, iodo, tosylate and mesylate, $R_1$ and $R_2$ are each a substituent selected from the group consisting of hydrogen, hydroxy, halogen, $C_1$ to $C_{10}$ straight-chain or branched alkyl, and $C_1$ to $C_{10}$ straight-chain or branched alkoxy, and $R_5$ is a substituent selected from the group consisting of hydrogen, $C_1$ to $C_{10}$ straight-chain or branched alkyl, pyridinyl and benzyl groups.).

Still yet another aspect of the present invention provides a method for preparing a compound represented by Chemical Formula A4 below, including reacting a compound represented by Chemical Formula A2 below and a compound represented by Chemical Formula B3 below in the presence of an organic solvent and a base catalyst (step 1), as shown in Reaction Scheme 3 below:

[Reaction Scheme 3]

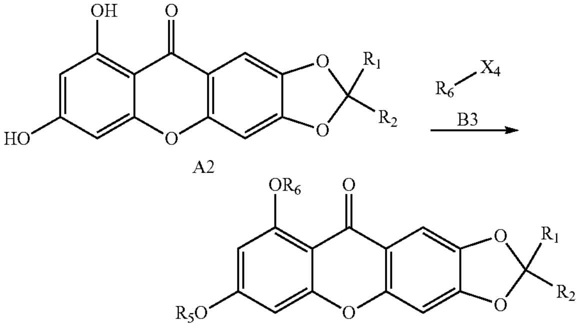

A2

A4

(in which, $X_4$ is each one of chloro, bromo, iodo, tosylate and mesylate, $R_1$ and $R_2$ are each a substituent selected from the group consisting of hydrogen, hydroxy, halogen, $C_1$ to $C_{10}$ straight-chain or branched alkyl, and $C_1$ to $C_{10}$ straight-chain or branched alkoxy, and $R_6$ is a substituent selected from the group consisting of hydrogen, $C_1$ to $C_{10}$ straight-chain or branched alkyl, pyridinyl and benzyl groups.).

Still yet another aspect of the present invention provides a method for preparing a compound represented by Chemical Formula A6 below, including reacting a compound represented by Chemical Formula A3 below and a compound represented by Chemical Formula B4 below in the presence of an organic solvent and a base catalyst (step 1), as shown in Reaction Scheme 4 below:

[Reaction Scheme 4]

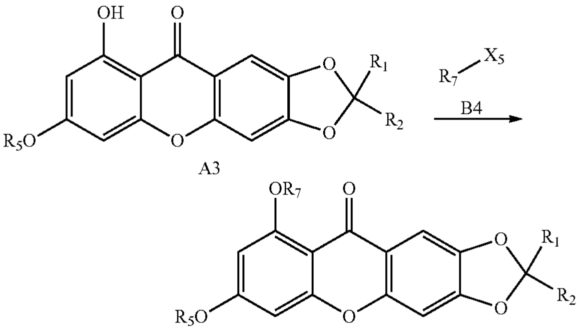

A3

A6

(in which, $X_5$ is each one of chloro, bromo, iodo, tosylate and mesylate, $R_1$ and $R_2$ are each a substituent selected from the group consisting of hydrogen, hydroxy, halogen, $C_1$ to $C_{10}$ straight-chain or branched alkyl, and $C_1$ to $C_{10}$ straight-chain or branched alkoxy, and $R_5$ and $R_7$ are each a substituent selected from the group consisting of hydrogen, $C_1$ to $C_{10}$ straight-chain or branched alkyl, pyridinyl and benzyl groups.).

Still yet another aspect of the present invention provides a method for preparing a compound represented by Chemical Formula A7 below, including reacting a compound represented by Chemical Formula A6 below and hydrogen gas in the presence of an organic solvent and a Pd/C catalyst (step 1), as shown in Reaction Scheme 5 below:

[Reaction Scheme 5]

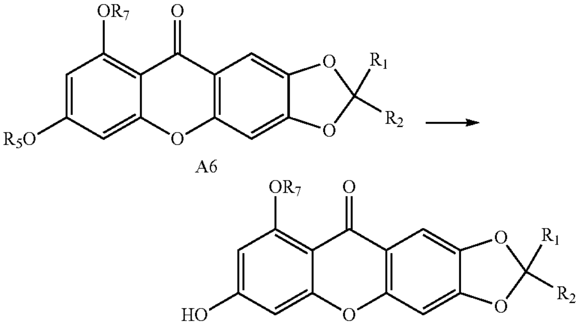

A6

A7

(in which, $R_1$ and $R_2$ are each a substituent selected from the group consisting of hydrogen, hydroxy, halogen, $C_1$ to $C_{10}$ straight-chain or branched alkyl, and $C_1$ to $C_{10}$ straight-chain or branched alkoxy, and $R_5$ and $R_7$ are each a substituent selected from the group consisting of hydrogen, $C_1$ to $C_{10}$ straight-chain or branched alkyl, pyridinyl and benzyl groups.).

Still yet another aspect of the present invention provides a method for preparing a compound represented by Chemical Formula A20 below, as shown in Reaction Scheme 6 below, including: synthesizing a compound represented by Chemical Formula A18-1 below by reacting a compound represented by Chemical Formula A18 below and a compound represented by Chemical Formula B5 below in the presence of an organic solvent and a base catalyst (step 1); synthesizing a compound represented by Chemical Formula A18-2 below by reacting a compound represented by Chemical Formula A18-1 below and a phosphate in the presence of an organic solvent (step 2); and reacting a compound represented by Chemical Formula A18-2 below and phosphorus oxychloride ($POCl_3$) in the presence of an organic solvent (step 3):

[Reaction Scheme 6]

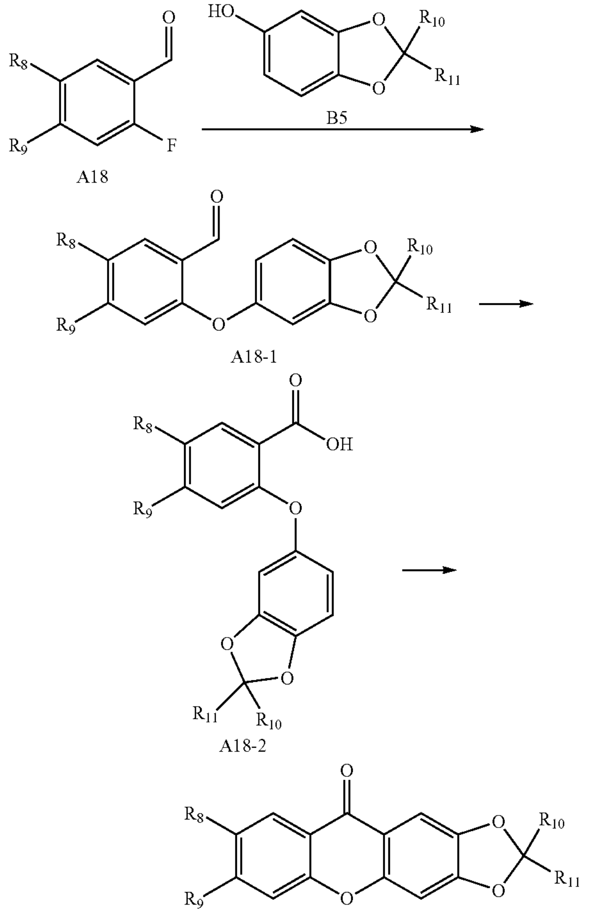

A18 B5 A18-1 A18-2 A20

(in which, $R_8$, $R_9$, $R_{10}$ and $R_{11}$ are each a substituent selected from the group consisting of hydrogen, hydroxy, halogen, $C_1$ to $C_{10}$ straight-chain or branched alkyl, and $C_1$ to $C_{10}$ straight-chain or branched alkoxy.).

Advantageous Effects

According to the present invention, the compound or the pharmaceutically acceptable salt thereof may inhibit mTORC1 activity and mTORC2 activity.

In addition, the compound or the pharmaceutically acceptable salt thereof may induce autophagy more excellently than rapamycin, a conventionally known mTORC1 inhibitor, and effectively remove Aβ accumulated in neurons.

In addition, the compound or the pharmaceutically acceptable salt thereof may restore memory and cognitive dysfunction in dementia model animals.

In addition, the compound or the pharmaceutically acceptable salt thereof may effectively reduce senile plaques and NFT in dementia model animals.

In addition, the compound or the pharmaceutically acceptable salt thereof may alleviate an inflammatory reaction occurring in the brain of dementia model animals.

In addition, the compound or the pharmaceutically acceptable salt thereof may promote neurogenesis in the hippocampus of dementia model animals.

Therefore, the novel compound of the present invention or the pharmaceutically acceptable salt thereof may be used as the pharmaceutical composition for preventing or treating neurodegenerative diseases, such as Alzheimer's disease, the pharmaceutical composition for prevention or treatment of mTORopathy, and/or the pharmaceutical composition for promoting neurogenesis.

BEST MODE FOR THE INVENTION

Hereinafter, the present invention will be described in detail.

An aspect of the present invention provides a compound represented by Chemical Formula A below or a pharmaceutically acceptable salt thereof:

[Chemical Formula A]

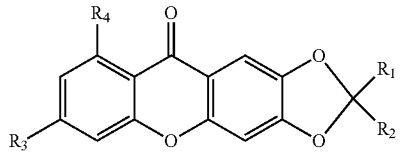

(in which, $R_1$ and $R_2$ are each a substituent selected from the group consisting of hydrogen, hydroxy, halogen, $C_1$ to $C_{10}$ straight-chain or branched alkyl, and $C_1$ to $C_{10}$ straight-chain or branched alkoxy, and $R_3$ and $R_4$ are each a substituent selected from the group consisting of hydrogen, hydroxy, halogen, $C_1$ to $C_{10}$ straight-chain or branched alkyl, $C_1$ to $C_{10}$ straight-chain or branched alkoxy, pyridinyl methoxy and benzyl oxy.).

In an embodiment of the present invention, $R_1$ and $R_2$ may be each hydrogen, and $R_3$ and $R_4$ may be each a substituent selected from the group consisting of hydrogen, $C_1$ to $C_{10}$ straight-chain or branched alkoxy, pyridinyl methoxy, and benzyl oxy.

In an embodiment of the present invention, the compound represented by Chemical Formula A may be one selected from the following compound group:

1) 7,9-dihydroxy-10H-[1,3]dioxolo[4,5-b]xanthen-10-one;
2) 9-hydroxy-7-methoxy-10H-[1,3]dioxolo[4,5-b]xanthen-10-one;
3) 7,9-dimethoxy-10H-[1,3]dioxolo[4,5-b]xanthen-10-one;
4) 7-(benzyloxy)-9-hydroxy-10H-[1,3]dioxolo[4,5-b]xanthen-10-one;
5) 7-(benzyloxy)-9-methoxy-10H-[1,3]dioxolo[4,5-b]xanthen-10-one;
6) 7-hydroxy-9-methoxy-10H-[1,3]dioxolo[4,5-b]xanthen-10-one;
7) 9-ethoxy-7-methoxy-10H-[1,3]dioxolo[4,5-b]xanthen-10-one;
8) 9-(benzyloxy)-7-methoxy-10H-[1,3]dioxolo[4,5-b]xanthen-10-one;
9) 9-hydroxy-7-(pyridin-4-ylmethoxy)-10H-[1,3]dioxolo[4,5-b]xanthen-10-one;
10) 10H-[1,3]dioxolo[4,5-b]xanthen-10-one;
11) 7-chloro-10H-[1,3]dioxolo[4,5-b]xanthen-10-one; and
12) 7-bromo-10H-[1,3]dioxolo[4,5-b]xanthen-10-one.

In an embodiment of the present invention, the compound represented by Chemical Formula A may be synthesized through sequential alkylation from norathyriol (1,3,6,7-tetrahydroxy-9H-xanthen-9-one) represented by Chemical Formula 1 below:

[Chemical Formula 1]

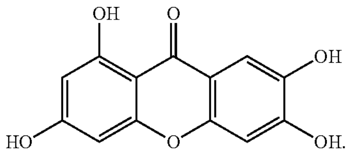

A detailed synthesis mechanism will be described below in the following aspect.

In an embodiment of the present invention, the compound represented by Chemical Formula A may inhibit activity of mammalian target of rapamycin complex 1 (mTORC1) or mammalian target of rapamycin complex 2 (mTORC2).

Figure 1:
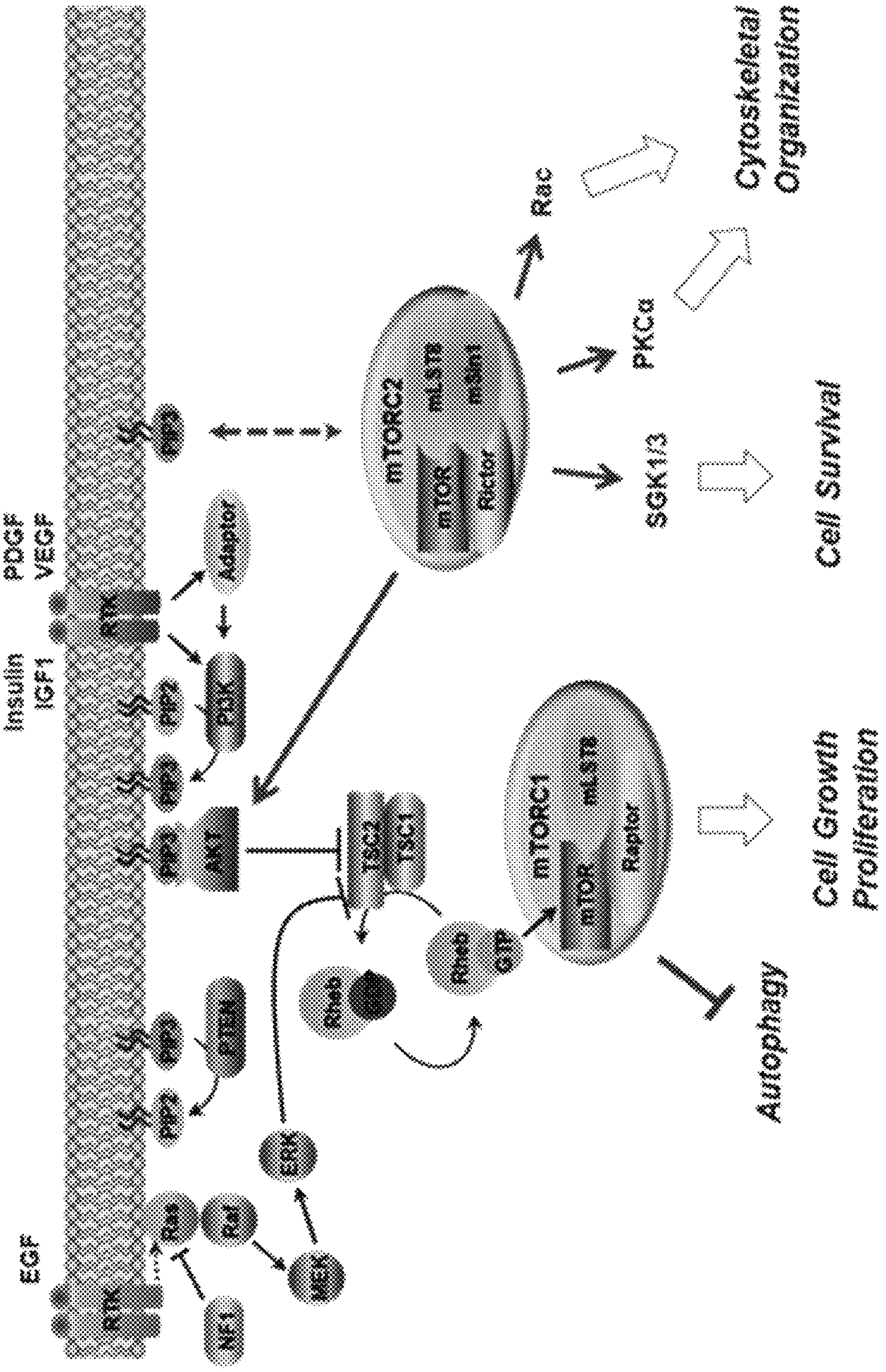
FIG. 1 is a summary diagram of an mTOR signaling pathway consisting of mTORC1 and mTORC2.

FIG. 1 is a summary diagram of mTORC1 and mTORC2 signaling pathways.

Referring to FIG. 1, it can be seen that a downstream signal transducer AKT of mTORC2 is activated by phosphorylation at Ser473 by mTORC2, and a downstream signal transducer S6K of mTORC1 is activated by phosphorylation at Thr389 by mTORC1 to promote cap-dependent protein synthesis and inactivate autophagy. Accordingly, when mTORC2 activity is inhibited, AKT activity is reduced, and as a result, the mTORC1 is inhibited, the cap-dependent protein synthesis is lowered, but the autophagy is activated.

The compound of the present invention may simultaneously inhibit AKT Ser473 phosphorylation and S6K Thr389 phosphorylation in human cells, and as a result, may inhibit mTORC1 and/or mTORC2 activity.

Another aspect of the present invention provides a pharmaceutical composition for preventing or treating neurodegenerative diseases, including the compound represented by Chemical Formula A of the aspect or the pharmaceutically acceptable salt thereof as an active ingredient.

In an embodiment of the present invention, the neurodegenerative disease may be at least one selected from the group consisting of dementia, Parkinson's disease, Alzheimer's disease, Pick's disease, Huntington's disease, epilepsy, stroke, apoplexy, ischemic brain disease, and memory loss, for example, Alzheimer's disease.

The preventive or therapeutic effect of the pharmaceutical composition of the present invention on neurodegenerative diseases will be described below in the following Examples.

Another aspect of the present invention provides a pharmaceutical composition for preventing or treating mTORopathy, including the compound represented by Chemical Formula A of the aspect or the pharmaceutically acceptable salt thereof as an active ingredient.

In an embodiment of the present invention, the mTORopathy may be at least one selected from the group consisting of epilepsy, autism spectrum disorder (ASD), macrocephaly, tuberous sclerosis complex (TSC), seizure, fragile X syndrome, or intellectual disability.

The preventive or therapeutic effect of the pharmaceutical composition of the present invention on mTORopathy will be described below in the following Examples.

Another aspect of the present invention provides a pharmaceutical composition for promoting neurogenesis, including the compound represented by Chemical Formula A of the aspect or the pharmaceutically acceptable salt thereof as an active ingredient.

The effect of promoting the neurogenesis of the pharmaceutical composition of the present invention will be described below in the following Examples.

Another aspect of the present invention provides a method for preparing a compound represented by Chemical Formula A2 below, including reacting norathyriol represented by Chemical Formula 1 below and a compound represented by Chemical Formula B1 below in the presence of an organic solvent and a base catalyst (step 1), as shown in Reaction Scheme 1 below:

[Reaction Scheme 1]

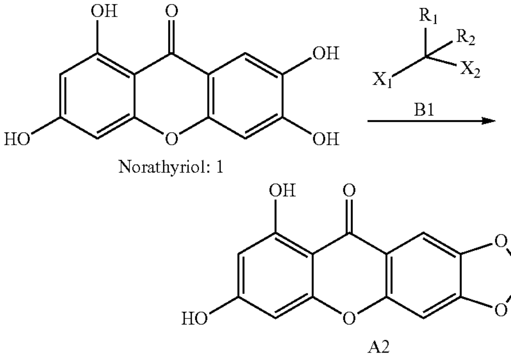

(in which, $X_1$ and $X_2$ are each one of chloro, bromo, iodo, tosylate and mesylate, and $R_1$ and $R_2$ are each a substituent selected from the group consisting of hydrogen, hydroxy, halogen, $C_1$ to $C_{10}$ straight-chain or branched alkyl, and $C_1$ to $C_{10}$ straight-chain or branched alkoxy.).

In an embodiment of the present invention, the organic solvent may be at least one selected from the group consisting of dimethyl sulfoxide, dimethyl formamide, acetone, tetrahydrofuran, benzene, toluene, ether, methanol, hexane, cyclohexane, pyridine, acetic acid, carbon tetrachloride, chloroform, dichloromethane, dichloroethane and water, and the base catalyst may be at least one selected from the group consisting of KOH, NaOH, $K_2CO_3$, $Na_2CO_3$, $KHCO_3$, $NaHCO_3$ and NaH.

In an embodiment of the present invention, the compound represented by Chemical Formula A2 prepared through Reaction Scheme 1 may be 7,9-dihydroxy-10H-[1,3]dioxolo[4,5-b]xanthen-10-one.

Another aspect of the present invention provides a method for preparing a compound represented by Chemical Formula A3 below, including reacting a compound represented by Chemical Formula A2 below and a compound represented by Chemical Formula B2 below in the presence of an organic solvent and a base catalyst (step 1), as shown in Reaction Scheme 2 below:

[Reaction Scheme 2]

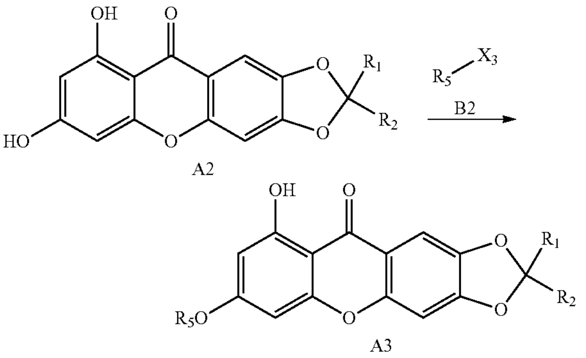

(in which, $X_3$ is each one of chloro, bromo, iodo, tosylate and mesylate, $R_1$ and $R_2$ are each a substituent selected from the group consisting of hydrogen, hydroxy, halogen, $C_1$ to $C_{10}$ straight-chain or branched alkyl, and $C_1$ to $C_{10}$ straight-chain or branched alkoxy, and $R_5$ is a substituent selected from the group consisting of hydrogen, $C_1$ to $C_{10}$ straight-chain or branched alkyl, pyridinyl and benzyl groups.).

In an embodiment of the present invention, the organic solvent may be at least one selected from the group consisting of dimethyl sulfoxide, dimethyl formamide, acetone, tetrahydrofuran, benzene, toluene, ether, methanol, hexane, cyclohexane, pyridine, acetic acid, carbon tetrachloride, chloroform, dichloromethane, dichloroethane and water, and the base catalyst may be at least one selected from the group consisting of KOH, NaOH, $K_2CO_3$, $Na_2CO_3$, $KHCO_3$, $NaHCO_3$ and NaH.

In an embodiment of the present invention, the compound represented by Chemical Formula A3 prepared through Reaction Scheme 2 may be 9-hydroxy-7-methoxy-10H-[1, 3]dioxolo[4,5-b]xanthen-10-one, 7-(benzyloxy)-9-hydroxy-10H-[1,3]dioxolo[4,5-b]xanthen-10-one, or 9-hydroxy-7-(pyridin-4-ylmethoxy)-10H-[1,3]dioxolo[4,5-b]xanthen-10-one.

Another aspect of the present invention provides a method for preparing a compound represented by Chemical Formula A4 below, including reacting a compound represented by Chemical Formula A2 below and a compound represented by Chemical Formula B3 below in the presence of an organic solvent and a base catalyst (step 1), as shown in Reaction Scheme 3 below:

[Reaction Scheme 3]

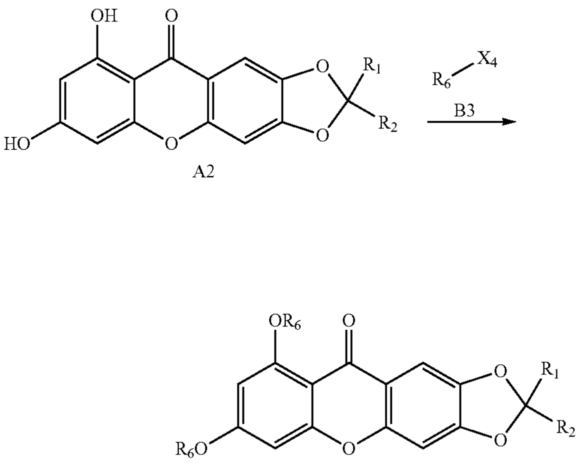
A2
B3
A4

(in which, $X_4$ is each one of chloro, bromo, iodo, tosylate and mesylate, $R_1$ and $R_2$ are each a substituent selected from the group consisting of hydrogen, hydroxy, halogen, $C_1$ to $C_{10}$ straight-chain or branched alkyl, and $C_1$ to $C_{10}$ straight-chain or branched alkoxy, and $R_6$ is a substituent selected from the group consisting of hydrogen, $C_1$ to $C_{10}$ straight-chain or branched alkyl, pyridinyl and benzyl groups.).

In an embodiment of the present invention, the organic solvent may be at least one selected from the group consisting of dimethyl sulfoxide, dimethyl formamide, acetone, tetrahydrofuran, benzene, toluene, ether, methanol, hexane, cyclohexane, pyridine, acetic acid, carbon tetrachloride, chloroform, dichloromethane, dichloroethane and water, and the base catalyst may be at least one selected from the group consisting of KOH, NaOH, $K_2CO_3$, $Na_2CO_3$, $KHCO_3$, $NaHCO_3$ and NaH.

In an embodiment of the present invention, the compound represented by Chemical Formula A4 prepared through Reaction Scheme 3 may be 7,9-dimethoxy-10H-[1,3]dioxolo[4,5-b]xanthen-10-one.

Another aspect of the present invention provides a method for preparing a compound represented by Chemical Formula A6 below, including reacting a compound represented by Chemical Formula A3 below and a compound represented by Chemical Formula B4 below in the presence of an organic solvent and a base catalyst (step 1), as shown in Reaction Scheme 4 below:

[Reaction Scheme 4]

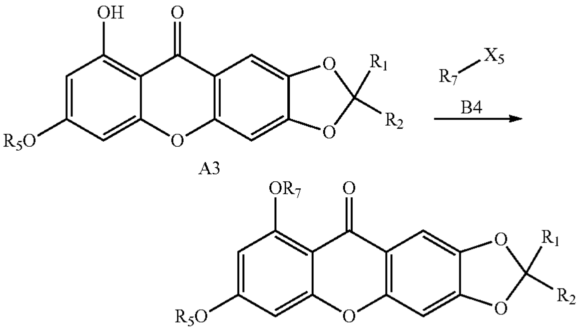
A3
B4
A6

(in which, $X_5$ is each one of chloro, bromo, iodo, tosylate and mesylate, $R_1$ and $R_2$ are each a substituent selected from the group consisting of hydrogen, hydroxy, halogen, $C_1$ to $C_{10}$ straight-chain or branched alkyl, and $C_1$ to $C_{10}$ straight-chain or branched alkoxy, and $R_5$ and $R_7$ are each a substituent selected from the group consisting of hydrogen, $C_1$ to $C_{10}$ straight-chain or branched alkyl, pyridinyl and benzyl groups.).

In an embodiment of the present invention, the organic solvent may be at least one selected from the group consisting of dimethyl sulfoxide, dimethyl formamide, acetone, tetrahydrofuran, benzene, toluene, ether, methanol, hexane, cyclohexane, pyridine, acetic acid, carbon tetrachloride, chloroform, dichloromethane, dichloroethane and water, and the base catalyst may be at least one selected from the group consisting of KOH, NaOH, $K_2CO_3$, $Na_2CO_3$, $KHCO_3$, $NaHCO_3$ and NaH.

In an embodiment of the present invention, the compound represented by Chemical Formula A6 prepared through Reaction Scheme 4 may be 7-(benzyloxy)-9-methoxy-10H-[1,3]dioxolo[4,5-b]xanthen-10-one, 9-ethoxy-7-methoxy-10H-[1,3]dioxolo[4,5-b]xanthen-10-one, or 9-(benzyloxy)-7-methoxy-10H-[1,3]dioxolo[4,5-b]xanthen-10-one.

Another aspect of the present invention provides a method for preparing a compound represented by Chemical Formula A7 below, including reacting a compound represented by Chemical Formula A6 below and hydrogen gas in the presence of an organic solvent and a Pd/C catalyst (step 1), as shown in Reaction Scheme 5 below:

[Reaction Scheme 5]

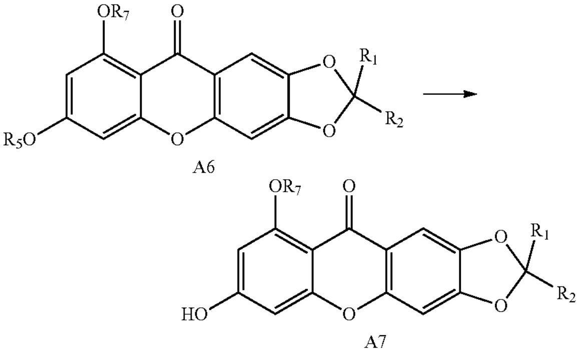
A6
A7

(in which, $R_1$ and $R_2$ are each a substituent selected from the group consisting of hydrogen, hydroxy, halogen, $C_1$ to $C_{10}$ straight-chain or branched alkyl, and $C_1$ to $C_{10}$ straight-chain or branched alkoxy, and $R_5$ and $R_7$ are each a substituent selected from the group consisting of hydrogen, $C_1$ to $C_{10}$ straight-chain or branched alkyl, pyridinyl and benzyl groups.).

In an embodiment of the present invention, the organic solvent may be at least one selected from the group consisting of dimethyl sulfoxide, dimethyl formamide, acetone, tetrahydrofuran, benzene, toluene, ether, methanol, hexane, cyclohexane, pyridine, acetic acid, carbon tetrachloride, chloroform, dichloromethane, dichloroethane and water, and the base catalyst may be at least one selected from the group consisting of KOH, NaOH, $K_2CO_3$, $Na_2CO_3$, $KHCO_3$, $NaHCO_3$ and NaH.

In an embodiment of the present invention, the compound represented by Chemical Formula A7 prepared through Reaction Scheme 5 may be 7-hydroxy-9-methoxy-10H-[1,3]dioxolo[4,5-b]xanthen-10-one.

Another aspect of the present invention provides a method for preparing a compound represented by Chemical Formula A20 below, as shown in Reaction Scheme 6, including synthesizing a compound represented by Chemical Formula A18-1 below by reacting a compound represented by Chemical Formula A18 below and a compound represented by Chemical Formula B5 below in the presence of an organic solvent and a base catalyst (step 1);

synthesizing a compound represented by Chemical Formula A18-2 below by reacting a compound represented by Chemical Formula A18-1 below and a phosphate in the presence of an organic solvent (step 2); and reacting a compound represented by Chemical Formula A18-2 below and phosphorus oxychloride ($POCl_3$) in the presence of an organic solvent (step 3):

[Reaction Scheme 6]

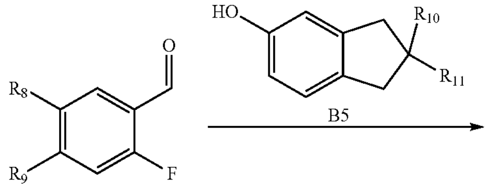

B5

A18

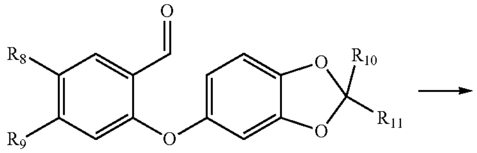

A18-1

-continued

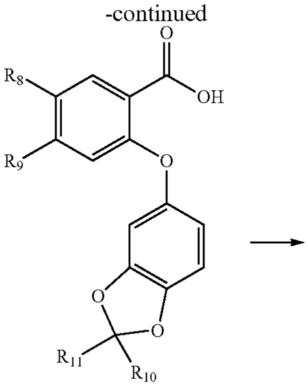

A18-2

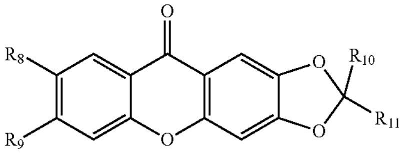

A20

(in which, $R_8$, $R_9$, $R_{10}$ and $R_{11}$ are each a substituent selected from the group consisting of hydrogen, hydroxy, halogen, $C_1$ to $C_{10}$ straight-chain or branched alkyl, and $C_1$ to $C_{10}$ straight-chain or branched alkoxy.).

In an embodiment of the present invention, the organic solvent may be at least one selected from the group consisting of dimethyl sulfoxide, dimethyl formamide, acetone, tetrahydrofuran, benzene, toluene, ether, methanol, hexane, cyclohexane, pyridine, acetic acid, carbon tetrachloride, chloroform, dichloromethane, dichloroethane and water, the base catalyst may be at least one selected from the group consisting of KOH, NaOH, $K_2CO_3$, $Na_2CO_3$, $KHCO_3$, $NaHCO_3$ and NaH, and the phosphate may be at least one selected from the group consisting of $K_4P_2O_7$, $KH_2PO_4$, $NaH_2PO_4$ and $Na_4P_2O_7$.

In an embodiment of the present invention, the compound represented by Chemical Formula A20 prepared through Reaction Scheme 6 may be 10H-[1,3]dioxolo[4,5-b]xanthen-10-one, 7-chloro-10H-[1,3]dioxolo[4,5-b]xanthen-10-one or 7-bromo-10H-[1,3]dioxolo[4,5-b]xanthen-10-one.

The present inventors identified that the compound of the present invention obtained by the method described above had effects of inhibiting the activities of mTORC1 and mTORC2 in human cells, promoting autophagy in primary cultured neurons, and inhibiting accumulation of senile plaques and NFT and suppressing brain immune responses in 5xFAD transgenic mice, which is a dementia animal model to be suitable for being used as a composition for preventing or treating nervous system diseases including Alzheimer's disease, mTORopathy caused by overactivation of the mTOR pathway, and neurodegenerative disease generated by abnormal proteostasis of proteins.

Definition

In the present invention, the "nervous system diseases" refer to nervous system diseases caused by overactivation of an mTOR signaling pathway or abnormal proteostasis of proteins.

In the present invention, the "nervous system diseases" include Alzheimer's disease in which the mTOR signaling pathway is overactivated and senile plaques and NFT formed by abnormal proteostasis of proteins are the main causes of disease.

In the present invention, the "nervous system disease" is a concept including mTORopathy as a genetic disease in which the mTOR signaling pathway is overactivated by germline or somatic mutations in neurons to cause neurological abnormalities, and may be any one selected from the group consisting of epilepsy (Moloney et al. (2021) Brain Comm. 3: 1-21), autism spectrum disorder (ASD) (Winden et al. (2018) Ann. Rev. Neurosci. 41: 1-23), macrocephaly (Butler et al., (2005) J. Med. Genet. 42: 318-321), tuberous sclerosis complex (TSC) (Crino (2015) Cold Spring Harb. Perspect. Med 5: a022442), seizure (Harvey et al. (2008) Epilepsia 49: 146-155), fragile X syndrome (Shanna et al. (2010) J. Neurosci. 30: 694-702), or intellectual disability (Dentel et al. (2019) Neuron 104: 1032-1033).

In the present invention, the "nervous system disease" is a concept including neurodegenerative diseases in which promoting proteostasis may be a causative treatment method, and may be any one selected from the group consisting of dementia (Sancesario & Bernardini (2018) Ann. Transl. Med. 6: 340), Parkinson's disease (Hague et al. (2005) J. Neural Neurosurg. Psychiatry 76: 1058-1063), Alzheimer's disease (Wenk (2003) J. Clinic. Psychiatry 64: 7-10), Pick's disease (Dickson (1998) Brain Pathol. 8: 339-354), or Huntington's disease (Hague et al. (2005) J. Neural Neurosurg. Psychiatry 76: 1058-1063).

Memory loss, traumatic central nervous system diseases, spinal cord injury diseases, peripheral nerve injuries, amyotrophic axonal sclerosis, or peripheral nerve diseases also accompany degeneration and death of neurons to expect a therapeutic effect when new neurogenesis is promoted, and accordingly, may be included in the 'nervous system diseases'.

Pharmaceutically Acceptable Salt

The active substance of the present invention may be used in the form of a pharmaceutically acceptable salt, and an acid addition salt formed by a pharmaceutically acceptable free acid is useful as the salt. The expression "pharmaceutically acceptable salt" refers to any organic or inorganic addition salt of a base compound of the active substance of which side effects caused by the salt do not reduce the beneficial effect at a concentration having a relatively non-toxic and harmless effective reaction to patients. These salts may use inorganic acids and organic acids as the free acid, the inorganic acid may use hydrochloric acid, hydrobromic acid, nitric acid, sulfuric acid, perchloric acid, phosphoric acid, or the like, and the organic acid may use citric acid, acetic acid, lactic acid, maleic acid, fumaric acid, gluconic acid, methanesulfonic acid, glycolic acid, succinic acid, tartaric acid, galacturonic acid, embonic acid, glutamic acid, aspartic acid, oxalic acid, (D) or (L) malic acid, maleic acid, methanesulfonic acid, ethanesulfonic acid, 4-toluenesulfonic acid, salicylic acid, citric acid, benzoic acid, malonic acid, or the like. In addition, these salts include alkali metal salts (sodium salt, potassium salt, etc.), alkaline earth metal salts (calcium salt, magnesium salt, etc.), and the like. For example, the acid addition salts may include acetate, aspartate, benzoate, besylate, bicarbonate/carbonate, bisulfate/sulfate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methyl sulfate, naphthylate, 2-naphsylate, nicotinate, nitrate, orotate, oxalate, palmitate, pamoate, phosphate/hydrogen phosphate/dihydrogen phosphate, saccharate, stearate, succinate, tartrate, tosylate, trifluoroacetate, aluminum, arginine, benzathine, calcium, choline, diethylamine, diolamine, glycine, lysine, magnesium, meglumine, olamine, potassium, sodium, tromethamine, zinc salts, etc., and preferably hydrochloride or trifluoroacetate among them.

The acid addition salt according to the present invention may be prepared by a conventional method, for example, a method of dissolving the active substance in an organic solvent such as methanol, ethanol, acetone, methylene chloride, acetonitrile, etc. and filtering and drying a precipitate produced by adding an organic or inorganic acid, or prepared by distilling the solvent and excess acid under reduced pressure, and then drying or crystallizing the mixture under an organic solvent.

In addition, the bases may also be used to prepare pharmaceutically acceptable metal salts. An alkali metal salt or an alkaline earth metal salt may be obtained, for example, by dissolving the compound in an excess alkali metal hydroxide or alkaline earth metal hydroxide solution, filtering a non-dissolved compound salt, and then evaporating and drying a filtrate. At this time, as the metal salt, it is pharmaceutically suitable to prepare a sodium, potassium or calcium salt. Further, silver salts corresponding thereto may be obtained by reacting the alkali metal or alkaline earth metal salt with a suitable silver salt (e.g., silver nitrate).

Furthermore, the present invention includes not only the active substance and a pharmaceutically acceptable salt thereof, but also all solvates, hydrates, isomers, optical isomers and the like that may be prepared therefrom.

Pharmaceutical Composition

The active substance of the present invention may be administered in various oral and parenteral formulations during clinical administration, and for formulations, may be prepared by using commonly used diluents or excipients, such as a filler, an extender, a binder, a wetting agent, a disintegrant, and a surfactant.

Solid formulations for oral administration include a tablet, a pill, a powder, a granule, a capsule, troche, and the like, and the solid formulations may be prepared by mixing at least one excipient, for example, starch, calcium carbonate, sucrose, lactose, gelatin, or the like with the active substance of the present invention. Further, lubricants such as magnesium stearate talc may be used in addition to simple excipients. Liquid formulations for oral administration may correspond to suspensions, oral liquids, emulsions, syrups, and the like, and may include various excipients, for example, a wetting agent, a sweetener, an aromatic agent, a preserving agent, and the like, in addition to water and liquid paraffin which are commonly used simple diluents.

Formulations for parenteral administration include a sterile aqueous solution, a non-aqueous solution, a suspension, an emulsion, a lyophilizing agent, and a suppository, and the like. As the non-aqueous solution and the suspension, propylene glycol, polyethylene glycol, vegetable oil such as olive oil, injectable ester such as ethyl oleate, and the like may be used. As a base of the suppository, witepsol, macrogol, Tween 61, cacao butter, laurinum, glycerol, gelatin, and the like may be used.

In addition, the effective dose for the human body of the active substance of the present invention may vary depending on the age, weight, sex, dosage form, health condition and disease degree of a patient, and may be generally about 0.001 to 100 mg/kg/day, preferably 0.01 to 35 mg/kg/day. Based on an adult patient with a body weight of 70 kg, the effective dose may be generally 0.07 to 7000 mg/day, preferably 0.7 to 2500 mg/day, and may be divided once or several doses a day at regular intervals according to the judgment of a doctor or pharmacist.

MODES FOR THE INVENTION

Examples

Synthesis and NMR Analysis of Compounds

Analytical Apparatus

To confirm the structures of compounds synthesized in Examples of the present invention, ADVANCE digital 500 was used for nuclear magnetic resonance spectrum ($^1H$ NMR), and $CD_3OD$ or DMSO-$d_6$ was used as a solvent. Mass spectra were used and displayed in an m/z form.

TLC and Column Chromatography

Thin layer chromatography (TLC) used silica gel (Merck F254) as a product of Merk Co., Ltd., and silica (Merck EM9385, 230-400 mesh) was used for column chromatography. In addition, in order to confirm materials separated on TLC, using a UV lamp (254 nm) or after dipping in an anisaldehyde coloring reagent, a plate was heated and confirmed.

Reagents

Reagents and solvents used in Examples of the present invention were purchased from Sigma-Aldrich and TCI products. Norathyriol used in the derivative synthesis was synthesized through a method of prior art KR 10-2004245 (method for preparing norathyriol using eco-friendly carbon-deglycosylation).

Example 1. Synthesis of 7,9-dihydroxy-10H-[1,3]dioxolo[4,5-b]xanthen-10-one (HN-1701(2))

A DMF (7 mL) solution of 500 mg (1.92 mmol, 1 equiv.) of norathyriol (1) was added with 694 mg (8.26 mmol, 4.3 equiv.) of $NaHCO_3$ and 0.28 mL (4.03 mmol, 2.1 equiv.) of dibromomethane at room temperature and then stirred at 80° C. for 4 hours. After cooling to room temperature, the reaction was terminated by adding water and ethyl acetate, and an organic layer was separated, washed with a 1 N aqueous hydrochloric acid solution, and then dried over anhydrous $MgSO_4$. After removing the solvents under vacuum, the reaction mixture was purified by column chromatography (silica gel) using a 20% methanol solvent in dichloromethane to obtain 401 mg (1.47 mmol, 77%) of HN-1701(2), and the reaction process was shown in Reaction Scheme 1-1 below:

[Reaction Scheme 1-1]

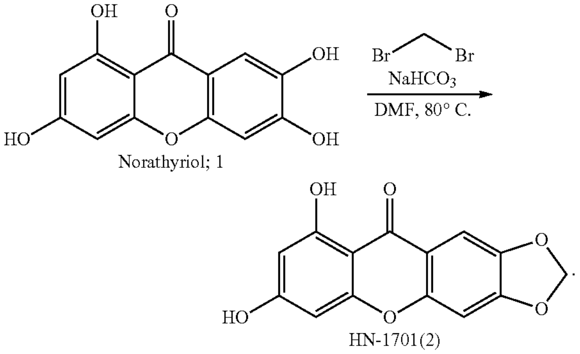

Norathyriol; 1

HN-1701(2)

MS m/z 273 (M+H$^+$)

$^1H$ NMR (500 MHz, DMSO-$d_6$) δ 12.95 (s, 1H), 7.41 (s, 1H), 7.24 (s, 1H), 6.32 (s, 1H), 6.23 (s, 2H), 6.15 (s, 1H)

Example 2. Synthesis of 9-hydroxy-7-methoxy-10H-[1,3]dioxolo[4,5-b]xanthen-10-one (HN-1702 (3))

An acetone (30 mL) solution of 167 mg (0.61 mmol, 1 equiv.) of HN-1701(2) synthesized in Example 1 was added with 106 mg (0.72 mmol, 1.3 equiv.) of $K_2CO_3$ and 0.06 mL (0.92 mmol, 1.5 equiv.) of iodomethane at room temperature and then stirred for 1 hour. The reaction solution was filtered and solvents were removed under vacuum. The mixture was purified by column chromatography (silica gel) using a 10% ethyl acetate solvent in n-hexane to obtain 58 mg (0.20 mmol, 33%) of HN-1702(3), and the reaction process was shown in Reaction Scheme 2-1 below:

[Reaction Scheme 2-1]

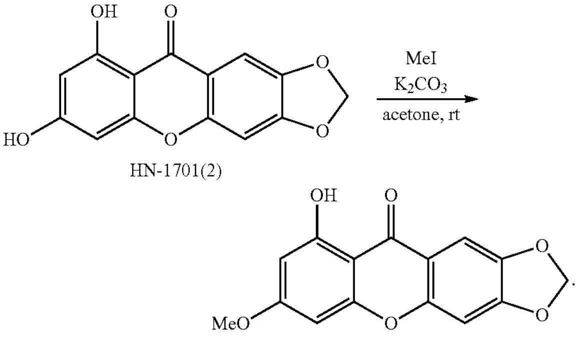

HN-1701(2)

HN-1702(3)

MS m/z 287 (M+H$^+$)

$^1H$ NMR (500 MHz, $CD_3OD$) δ 7.48 (s, 1H), 7.02 (s, 1H), 6.53 (d, 1H, J=2.8 Hz), 6.34 (d, 1H, J=2.9 Hz), 6.16 (s, 2H), 3.90 (s, 3H)

Example 3. Synthesis of 7-(benzyloxy)-9-hydroxy-10H-[1,3]dioxolo[4,5-b]xanthen-10-one (HN-2101 (5))

20 mg (0.073 mmol, 1 equiv.) of HN-1701(2) prepared in Example 1, 18.9 mg (0.110 mmol, 1.5 equiv.) of benzyl bromide, and 12.7 mg (0.091 mmol, 1.25 equiv.) of $K_2CO_3$ were dissolved in 2.3 mL of DMF, and then stirred at room temperature for 24 hours. Thereafter, the reaction solution was filtered, the solvent was removed from a filtrate under vacuum, and then the reaction product was purified by column chromatography (silica gel) using a 25% ethyl acetate solvent in n-hexane to obtain 16 mg (0.049 mmol, 68%) of a target compound HN-2101(5), and the reaction process was shown in Reaction Scheme 2-2 below:

[Reaction Scheme 2-2]

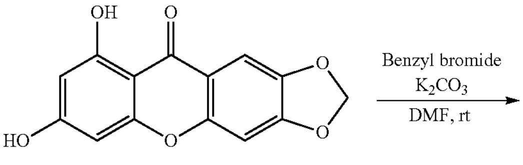

HN-1701(2)

-continued

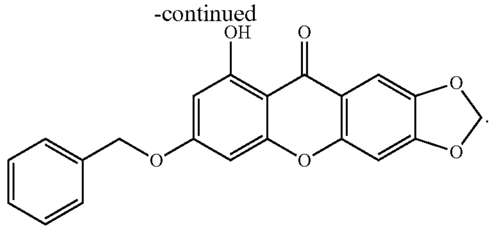

HN-2101(5)

MS m/z 363 (M+H$^+$)

$^1$H NMR (500 MHz, DMSO-$d_6$) δ 12.94 (s, 1H), 7.40-7.48 (m, 5H), 7.37 (s, 1H), 7.26 (s, 1H), 6.67 (s, 1H), 6.47 (s, 1H), 6.25 (s, 2H), 5.25 (s, 2H)

Example 4. Synthesis of 9-hydroxy-7-(pyridin-4-ylmethoxy)-10H-[1,3]dioxolo[4,5-b]xanthen-10-one (HN-2108(10))

30 mg (0.110 mmol, 1 equiv.) of HN-1701(2) prepared in Example 1 was dissolved in 4 ml, of DMF, and then added with 45.6 mg (0.330 mmol, 3 equiv.) of $K_2CO_3$ and 1.8 mg (0.011 mmol, 0.1 equiv.) of KI in an ice bath and stirred. After 1 hour, the mixture was added with 23.5 mg (0.143 mmol, 1.3 equiv.) of 4-(chloromethyl)pyridine and stirred at room temperature for 18 hours. The reaction was terminated by adding $H_2O$ and extracted with ethyl acetate. An organic layer was washed with water and brine, and then dried with anhydrous $MgSO_4$ and concentrated in vacuum. The reaction mixture was purified by column chromatography (silica gel) using a 50% ethyl acetate solvent in dichloromethane to obtain 13.8 mg (0.038 mmol, 35%) of a target compound HN-2108(10), and the reaction process was shown in Reaction Scheme 2-3 below:

[Reaction Scheme 2-3]

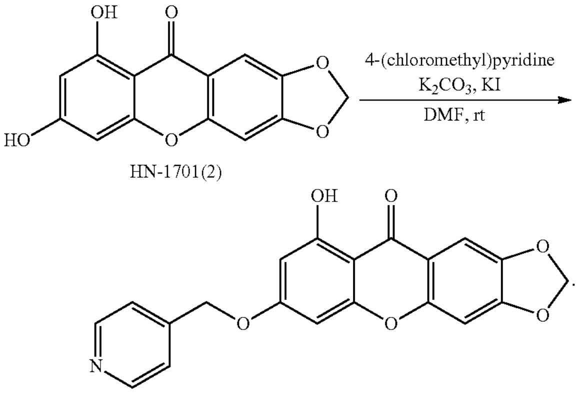

HN-1701(2)

HN-2108(10)

MS m/z 364 (M+H$^+$)

$^1$H NMR (500 MHz, DMSO) δ 8.58 (d, J=1.6 Hz, 1H), 8.57 (d, J=1.6 Hz, 1H), 7.44 (s, 1H), 7.42 (s, 2H), 7.26 (s, 1H), 6.67 (d, J=2.3 Hz, 1H), 6.48 (d, J=2.3 Hz, 1H), 6.23 (s, 2H), 5.33 (s, 2H)

Example 5. Synthesis of 7,9-dimethoxy-10H-[1,3]dioxolo[4,5-b]xanthen-10-one (HN-1703(4))

A DMF (3 mL) solution of 140 mg (0.51 mmol, 1 equiv.) of HN-1701(2) prepared in Example 1 was added with 61 mg (1.53 mmol, 3 equiv.) of 60% NaH in mineral oil at 0° C. and then stirred for 30 minutes. After 30 minutes, the mixture was added with 0.13 mL (2.04 mmol, 4 equiv.) of iodomethane and stirred at room temperature for 1 hour, and then added with saturated aqueous ammonia chloride to terminate the reaction, and added with water and ethyl acetate. An organic layer was separated, washed with brine, and dried over anhydrous $MgSO_4$. After removing the solvents under vacuum, the reaction mixture was purified by column chromatography (silica gel) using a 50% ethyl acetate solvent in dichloromethane to obtain 50 mg (0.17 mmol, 33%) of HN-1703(4), and the reaction process was shown in Reaction Scheme 3-1 below:

[Reaction Scheme 3-1]

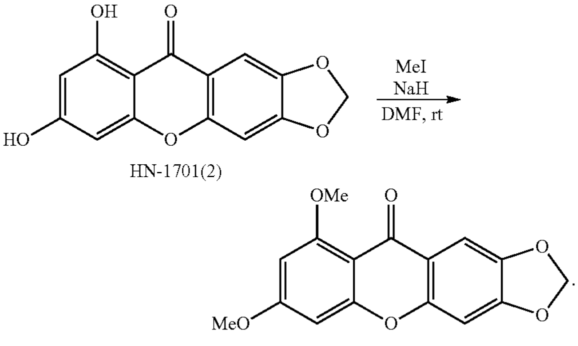

HN-1701(2)

HN-1703(4)

MS m/z 301 (M+H$^+$)

$^1$H NMR (500 MHz, $CD_3OD$) 7.49 (s, 1H), 6.96 (s, 1H), 6.65 (d, 1H, J=2.8 Hz), 6.51 (d, 1H, J=2.9 Hz), 6.13 (s, 2H), 3.94 (s, 3H), 3.94 (s, 3H).

Example 6. Synthesis Method of 7-(benzyloxy)-9-methoxy-10H-[1,3]dioxolo[4,5-b]xanthen-10-one (HN-2102(6))

150 mg (0.414 mmol, 1 equiv.) of HN-2101(5) prepared in Example 3 and 49.7 mg (1.242 mmol, 3 equiv.) of 60% NaH in mineral oil were dissolved in 20 mL of DMF, and then stirred in an ice bath. After 1 hour, the mixture was added with 0.1 mL (1.656 mmol, 4 equiv.) of iodomethane and stirred at room temperature for 16 hours. The reaction was terminated by adding $H_2O$ and extracted with ethyl acetate. An organic layer was washed with water and brine, dried over anhydrous $MgSO_4$, and then the reaction solution was filtered and the solvent was removed from the filtrate under vacuum. The reaction mixture was purified by column chromatography (silica gel) using a 5% ethyl acetate solvent in dichloromethane to obtain 135 mg (0.360 mmol, 87%) of a target compound HN-2102(6), and the reaction process was shown in Reaction Scheme 4-1 below:

[Reaction Scheme 4-1]

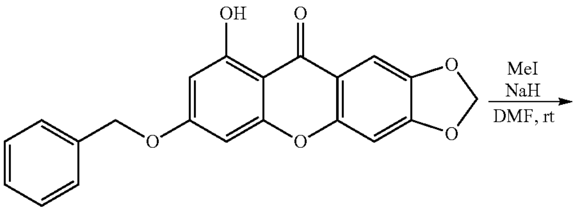

HN-2101(5)

-continued

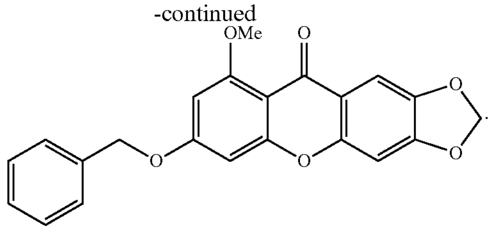

HN-2102(6)

MS m/z 377 (M+H$^+$)

$^1$H NMR (500 MHz, DMSO-$d_6$) δ 7.36-7.52 (m, 5H), 7.35 (s, 1H), 7.14 (s, 1H), 6.72 (d, J=2.3 Hz, 1H), 6.58 (d, J=2.3, 1H), 6.19 (s, 2H), 5.26 (s, 2H), 3.85 (s, 3H)

Example 7. Synthesis Method of 9-ethoxy-7-methoxy-10H-[1,3]dioxolo[4,5-b]xanthen-10-one (HN-2104(8))

A DMF (4 mL) solution of 25.4 mg (0.088 mmol, 1 equiv.) of HN-1702(3) prepared in Example 2 was added with 0.6 mg (0.265 mmol, 3 equiv.) of 60% NaH in mineral oil. After stirring for 1 hour, the mixture was added with 55.3 mg (0.354 mmol, 4 equiv.) of iodomethane and stirred at room temperature for 16 hours. The reaction was terminated by adding $H_2O$ and extracted with ethyl acetate. An organic layer was washed with water and brine, dried over anhydrous $MgSO_4$, and then the reaction solution was filtered and the solvent was removed from the filtrate under vacuum. The reaction mixture was purified by column chromatography (silica gel) using a 25% ethyl acetate solvent in n-hexane to obtain 23.9 mg (0.076 mmol, 86%) of a target compound HN-2104(8), and the reaction process was shown in Reaction Scheme 4-2 below:

[Reaction Scheme 4-2]

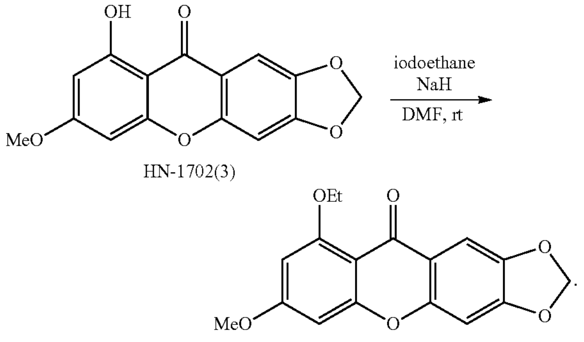

HN-1702(3)

HN-2104(8)

MS m/z 315 (M+H$^+$)

$^1$H NMR (500 MHz, DMSO) δ 7.34 (s, 1H), 7.09 (s, 1H), 6.59 (s, 1H), 6.44 (s, 1H), 6.16 (s, 2H), 4.07 (q, 2H), 3.85 (s, 3H), 2.47 (s, 3H),

Example 8. Synthesis Method of 9-(benzyloxy)-7-methoxy-10H-[1,3]dioxolo[4,5-b]xanthen-10-one (HN-2105(9))

A DMF (4 mL) solution of 21 mg (0.073 mmol, 1 equiv.) of HN-1702(3) prepared in Example 2 was added with 8.8 mg (0.220 mmol, 3 equiv.) of 60% NaH in mineral oil. After stirring for 1 hour, the mixture was added with 43.2 mg (0.293 mmol, 4 equiv.) of benzyl bromide and stirred at room temperature for 16 hours. The reaction was terminated by adding $H_2O$ and extracted with ethyl acetate. An organic layer was washed with water and brine, dried over anhydrous $MgSO_4$, and then the reaction solution was filtered and the solvent was removed from the filtrate under vacuum. The reaction mixture was purified by column chromatography (silica gel) using a dichloromethane solvent to obtain 26.6 mg (0.071 mmol, 97%) of a target compound HN-2105(9), and the reaction process was shown in Reaction Scheme 4-3 below:

[Reaction Scheme 4-3]

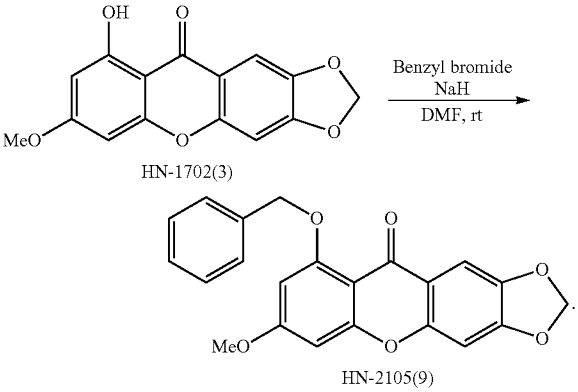

HN-1702(3)

HN-2105(9)

MS m/z 377 (M+H$^+$)

$^1$H NMR (500 MHz, DMSO) δ 7.38-7.68 (m, 5H), 7.28 (s, 1H), 7.11 (s, 1H), 6.64 (d, J=2.3 Hz, 1H), 6.59 (d, J=2.3 Hz, 1H), 6.17 (s, 2H), 5.22 (s, 2H), 3.87 (s, 3H)

Example 9. Synthesis Method of 7-hydroxy-9-methoxy-10H-[1,3]dioxolo[4,5-b]xanthen-10-one (HN-2103(7))

125 mg (0.332 mmol, 1 equiv.) of HN-2102(6) prepared in Example 6 was dissolved in 30 mL of MeOH, added with a catalytic amount of 10% Pd/C, and then stirred under a hydrogen atmosphere for 24 hours. The reaction solution was filtered with celite to remove the catalyst, and then the solvent was removed from the filtrate under vacuum. The reaction mixture was purified by column chromatography (silica gel) using an ethyl acetate solvent to obtain 20 mg (0.069 mmol, 19%) of a target compound HN-2103(7), and the reaction process was shown in Reaction Scheme 5-1 below:

[Reaction Scheme 5-1]

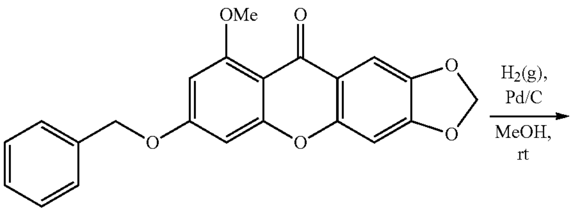

HN-2102(6)

-continued

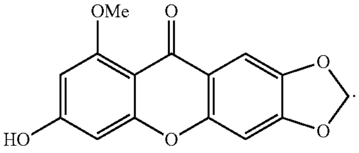

HN-2103(7)

MS m/z 287 (M+H$^+$)

$^1$H NMR (500 MHz, DMSO-d$_6$) δ 7.33 (s, 1H), 7.12 (s, 1H), 6.38 (s, 1H), 6.35 (s, 1H), 6.17 (s, 2H), 3.81 (s, 3H)

Examples 10 to 12

General Synthesis Method

As shown in Reaction Scheme 6A below, 1.3 equiv. of $K_2CO_3$ was added to a DMF solution of 1 equiv. of fluorobenzaldehyde (A18) and 1.2 equiv. of phenol (B5), and then stirred at 100° C. for 16 hours. The reaction was terminated with a 1 N HCl solution and extracted with ethyl acetate. An organic layer was washed with water and brine, and then dried with anhydrous $MgSO_4$ and the filtrate was concentrated in vacuum. The reaction mixture was purified by column chromatography (silica gel) to obtain a biaryl compound (A18-1).

1.5 equiv. of a $NaClO_2$ aqueous solution was slowly added dropwise to a DMSO solution of 1 equiv. of a biaryl compound (A18-1) and 1.1 equiv. of $NaH_2PO_4$ for 30 minutes. After 2 hours, the reaction was terminated by adding a $NaHCO_3$ solution, acidified with a 1 N HCl solution, and then extracted with ethyl acetate. The organic layer was washed with water and a 1 N HCl solution, dried over anhydrous $MgSO_4$, and filtered. The solvent was removed from the filtrate under vacuum, and then the reaction mixture was purified by column chromatography (silica gel) to obtain benzoic acid (A18-2).

A 1,2-dichloroethane solution of the 1 equiv. of benzoic acid (A18-2) was added with 3 equiv. of $POCl_3$, and then heated to reflux. After 24 hours, the reaction was terminated by adding an $NaHCO_3$ solution at room temperature, and extracted with dichloromethane. The organic layer was washed with water, dried over anhydrous $MgSO_4$, and filtered and the solvent was removed from the filtrate under vacuum. The reaction mixture was purified by column chromatography (silica gel) to obtain a target xanthone (A20) compound.

[Reaction Scheme 6A]

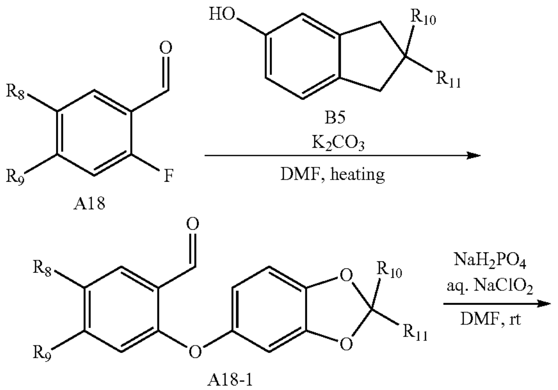

A18

A18-1

-continued

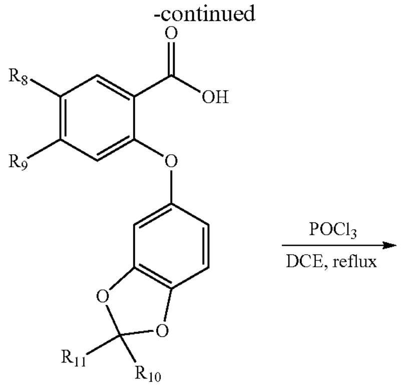

A18-2

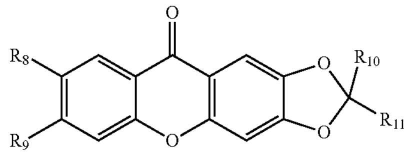

A20

(in which, $R_8$, $R_9$, $R_{10}$ and $R_{11}$ are each a substituent selected from the group consisting of hydrogen, hydroxy, halogen, $C_1$ to $C_{10}$ straight-chain or branched alkyl, and $C_1$ to $C_{10}$ straight-chain or branched alkoxy.)

Example 10. Synthesis Method of 10H-[1,3]dioxolo[4,5-b]xanthen-10-one (HN-2110(20))

A target compound HN-2110(20) was obtained from 2-fluorobenzaldehyde(18) and sesamol(19) using the general synthesis method, and the reaction process was shown in Reaction Scheme 6A-1 below:

[Reaction Scheme 6A-1]

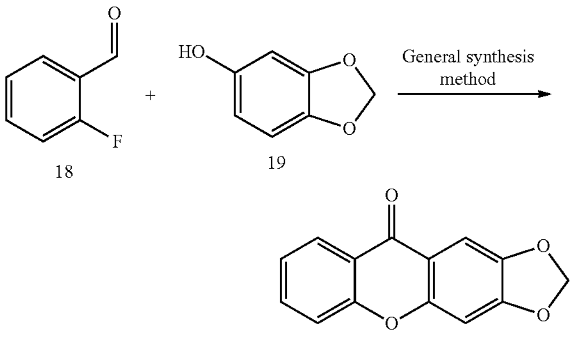

18

19

HN-2110 (20)

MS m/z 241 (M+H$^+$)

$^1$H NMR (500 MHz, $CDCl_3$) δ 8.31 (d, J=7.9 Hz, 1H), 7.74-7.62 (m, 2H), 7.44 (d, J=8.5 Hz, 1H), 7.36 (t, J=7.5 Hz, 1H), 6.89 (s, 1H), 6.10 (s, 2H)

Example 11. Synthesis Method of 7-chloro-10H-[1,3]dioxolo[4,5-b]xanthen-10-one (HN-2117(28))

A target compound HN-2117(28) was obtained from 4-chloro-2-fluorobenzaldehyde(26) and sesamol(27) using the general synthesis method, and the reaction process was shown in Reaction Scheme 6A-2 below.

[Reaction Scheme 6A-2]

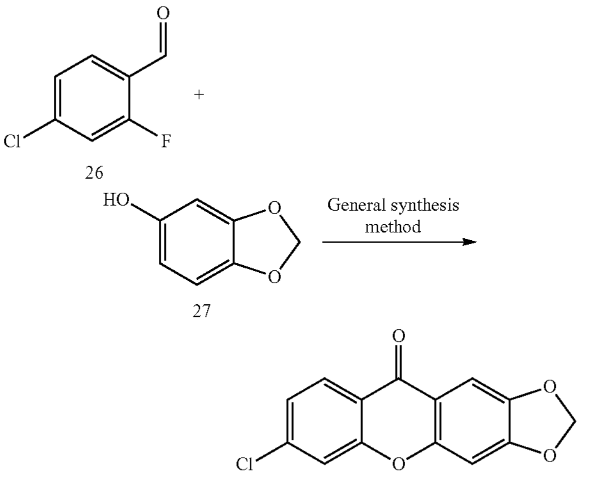

HN-2117 (28)

MS m/z 275 (M+H$^+$)

$^1$H NMR (500 MHz, $CDCl_3$) δ 8.25 (d, J=8.5 Hz, 1H), 7.63 (s, 1H), 7.48 (s, 1H), 7.34 (d, J=8.5 Hz, 1H), 6.89 (s, 1H), 6.12 (s, 2H)

Example 12. Synthesis Method of 7-bromo-10H-[1,3]dioxolo[4,5-b]xanthen-10-one (HN-2122(30))

A target compound HN-2122(30) was obtained from 4-bromo-2-fluorobenzaldehyde(29) and sesamol(27) using the general synthesis method, and the reaction process was shown in Reaction Scheme 6A-3 below.

[Reaction Scheme 6A-3]

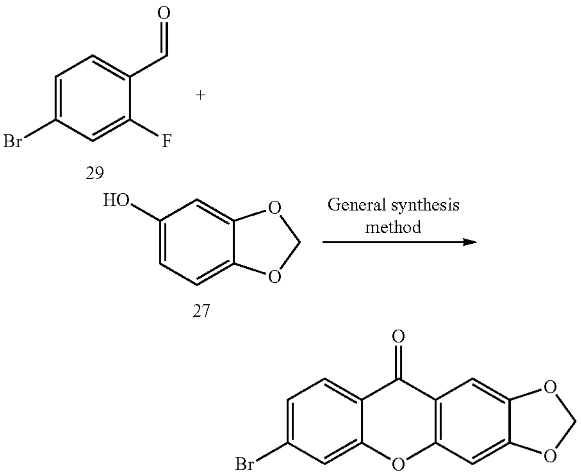

HN-2122 (30)

MS m/z 320 (M+H$^+$)

$^1$H NMR (500 MHz, $CDCl_3$) δ 8.17 (d, J=8.7 Hz, 1H), 7.66 (s, 1H), 7.63 (s, 1H), 7.49 (d, J=8.4 Hz, 1H), 6.89 (s, 1H), 6.12 (s, 2H).

The compounds synthesized in Examples 1 to 12 were shown in Table 1 below:

TABLE 1

| | Structure | Name |
|---|---|---|
| Example 1 (HN-1701(2)) | 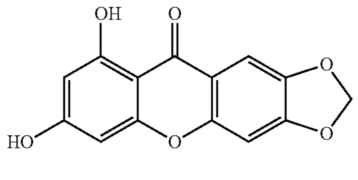 [SMILES: O=c1c2cc3c(cc2oc2cc(O)cc(O)c12)OCO3] HN-1701(2) | 7,9-dihydroxy-10H-[1,3]dioxolo[4,5-b]xanthen-10-one |
| Example 2 (HN-1702(3)) | 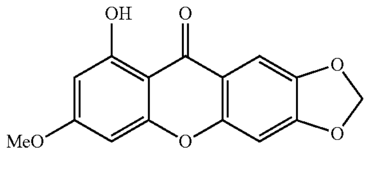 [SMILES: COc1cc(O)c2c(=O)c3cc4c(cc3oc2c1)OCO4] HN-1702(3) | 9-hydroxy-7-methoxy-10H-[1,3]dioxolo[4,5-b]xanthen-10-one |
| Example 3 (HN-2101(5)) | 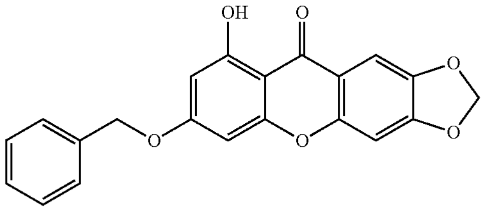 [SMILES: O=c1c2cc3c(cc2oc2cc(OCc4ccccc4)cc(O)c12)OCO3] HN-2101(5) | 7-(benzyloxy)-9-hydroxy-10H-[1,3]dioxolo[4,5-b]xanthen-10-one |

TABLE 1-continued

| | Structure | Name |
|---|---|---|
| Example 4 (HN-2108(10)) | 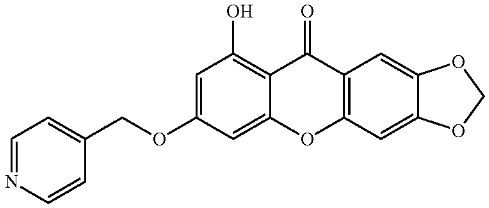 [SMILES: O=c1c2cc3c(cc2oc2cc(OCc4ccncc4)cc(O)c12)OCO3] HN-2108(10) | 9-hydroxy-7-(pyridin-4-ylmethoxy)-10H-[1,3]dioxolo[4,5-b]xanthen-10-one |
| Example 5 (HN-1703(4)) | 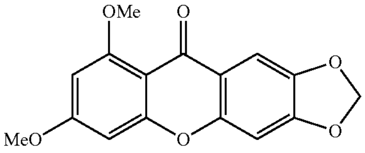 [SMILES: COc1cc(OC)c2c(=O)c3cc4c(cc3oc2c1)OCO4] HN-1703(4) | 7,9-dimethoxy-10H-[1,3]dioxolo[4,5-b]xanthen-10-one |
| Example 6 (HN-2102(6)) | 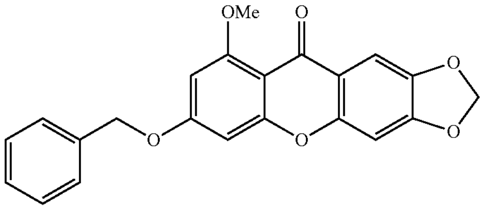 [SMILES: COc1cc(OCc2ccccc2)cc2oc3cc4c(cc3c(=O)c12)OCO4] HN-2102(6) | 7-(benzyloxy)-9-methoxy-10H-[1,3]dioxolo[4,5-b]xanthen-10-one |
| Example 7 (HN-2104(8)) | 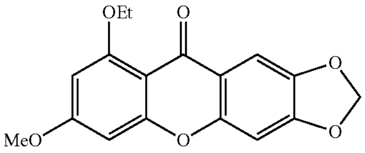 HN-2104(8) | 9-ethoxy-7-methoxy-10H-[1,3]dioxolo[4,5-b]xanthen-10-one |
| Example 8 (HN-2105(9)) | 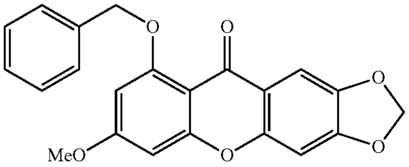 [SMILES: COc1cc(OCc2ccccc2)c2c(=O)c3cc4c(cc3oc2c1)OCO4] HN-2105(9) | 9-(benzyloxy)-7-methoxy-10H-[1,3]dioxolo[4,5-b]xanthen-10-one |
| Example 9 (HN-2103(7)) | 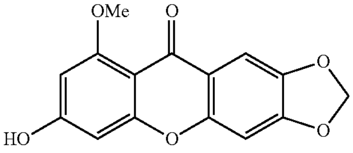 HN-2103(7) | 7-hydroxy-9-methoxy-10H-[1,3]dioxolo[4,5-b]xanthen-10-one |
| Example 10 (HN-2110(20)) | 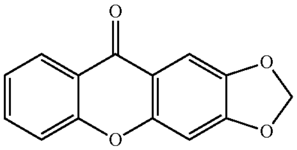 [SMILES: O=c1c2ccccc2oc2cc3c(cc12)OCO3] HN-2110(20) | 10H-[1,3]dioxolo[4,5-b]xanthen-10-one |

TABLE 1-continued

| | Structure | Name |
|---|---|---|
| Example 11 (HN-2117(28)) | 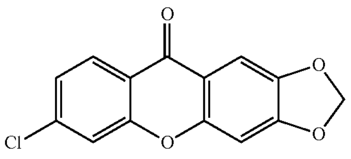 [SMILES: O=c1c2ccc(Cl)cc2oc2cc3c(cc12)OCO3] (HN-2117(28)) | 7-chloro-10H-[1,3]dioxolo[4,5-b]xanthen-10-one |
| Example 12 (HN-2122(30)) | 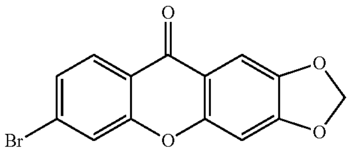 [SMILES: O=c1c2ccc(Br)cc2oc2cc3c(cc12)OCO3] HN-2122(30) | 7-bromo-10H-[1,3]dioxolo[4,5-b]xanthen-10-one |

EXPERIMENTAL EXAMPLES

Evaluation of In Vitro Efficacy of Compounds

Experimental Example 1. Evaluation of mTORC1 Inhibition Ability and mTORC2 Inhibition Ability Method HeLa cells were cultured in DMEM (Dulbecco's Modified Eagles Media) containing 10% FBS, penicillin (100 units/ml), and streptomycin (100 μg/ml) at 37° C. in a 5% $CO_2$ incubator. Culture was started by seeding $4\times10^5$ cells in a 100 mm culture dish, and subcultured every 3 days.

Immunoblot analysis was performed by the following method. SDS-PAGE-developed proteins were electroblotted and transferred and a PVDF membrane was blocked by shaking for 1 hour in a TBS-T buffer (20 mM Tris, 137 mM NaCl, 0.1% Tween 20) containing 5% skim milk. The membrane was repeatedly washed with a TBS-T buffer three times for 5 minutes, and reacted with a first antibody diluted in a TBS-T buffer containing 5% skim milk or 5% BSA overnight at 4° C. Thereafter, the membrane was repeatedly washed with a TBS-T buffer three times for 5 minutes, and reacted with a second antibody diluted in a TBS-T buffer containing 5% skim milk for 30 minutes at room temperature. The membrane was repeatedly washed with a TBS-T buffer containing 5% skim milk five times for 5 minutes, and then protein bands bound to the second antibody were detected by a chemiluminescence method. As the first antibody, Akt (Cell signalling, #4691), pAkt(S473) (Cell signalling, #4060), p70S6K (Cell signalling, #S6198), and pp70S6K(T389) (Cell signalling, #9205S) were used, and as the second antibody, HRP-conjugated anti-rabbit (#711-035-152, Jackson immunoresearch laboratory) and HRP-conjugated anti-mouse IgG (#515-035-072, Jackson immunoresearch laboratory) were used.

Results

Figure 2A:
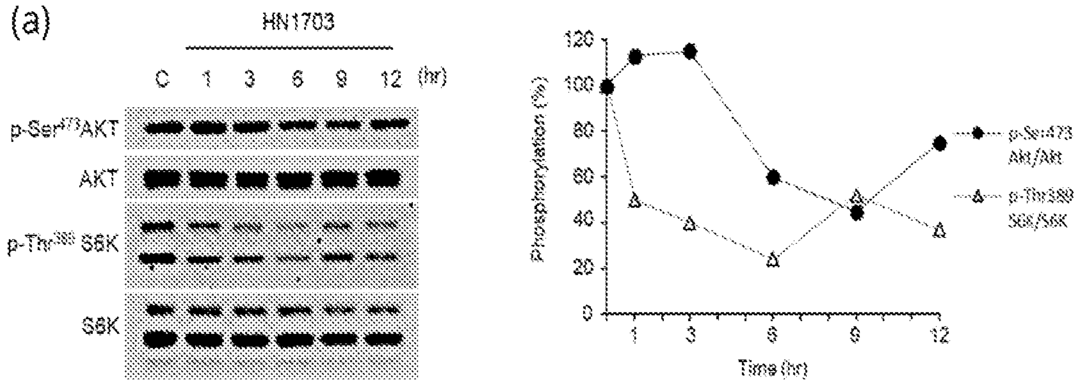
FIGS. 2A to 2C show immunoblot analysis results showing that a compound of an embodiment of the present invention inhibits mTORC1 activity and mTORC2 activity in HeLa cells as a human cell line.

The HN-1703 synthesized in Example 5 was treated using a human cell line HeLa, and then changes in phosphorylation of S6K Thr389, a marker of mTORC1 activity, and changes in phosphorylation of AKT Ser473, a marker of mTORC2 activity, were examined by immunoblot analysis and illustrated in FIG. 2A.

Referring to FIG. 2A, it was confirmed that at 40 M, HN-1703 inhibited the mTORC1 activity by 48% compared to the control group and the mTORC2 activity by 55% compared to the control group.

Figure 2B:
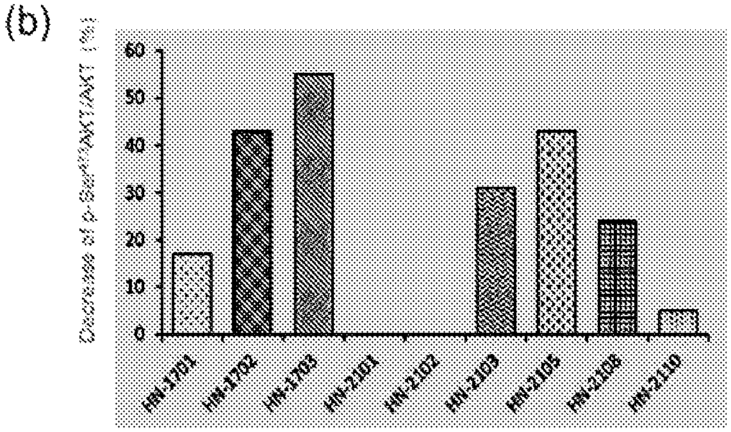
Figure 2C:
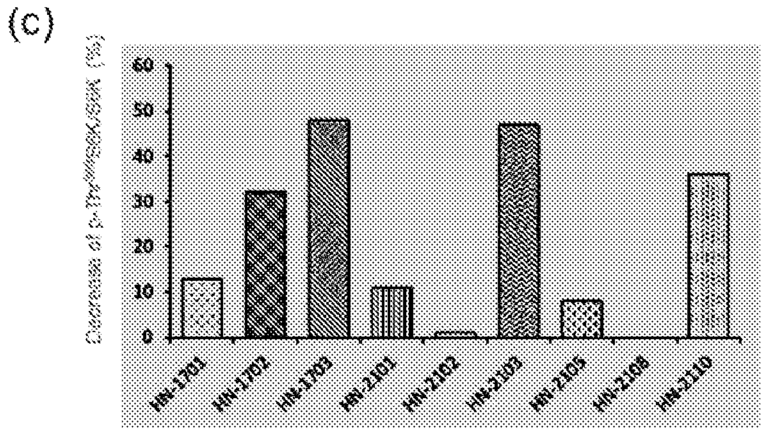

Referring to FIG. 2B, it was confirmed that among the compounds synthesized in Examples 1 to 12, HN-1701, HN-1702, HN-1703, HN-2103, HN-2105, and HN-2108 inhibited the mTORC2 activity by 25% to 40% compared to the control group, and HN-1701, HN-1702, HN-1703, HN-2103 and HN-2110 inhibited the mTORC1 activity by 15% to 50% compared to the control group.

Experimental Example 2. Evaluation of Autophagy Promotion Efficacy in Primary Cultured Neurons Method Primary neurons culture was performed from the hippocampus of rat (SD, Orient Bio) embryonic 16-day (E16) embryos. The left and right hemispheres of the extracted brain were separated using sterile tweezers under a dissecting microscope, the meninges were peeled off, the hippocampus was cut with No. 55 tweezers, and neural progenitor cells were mechanically dissolved in a $Ca^{2+}/Mg^{2+}$-free HBSS (Invitrogen) solution by pipetting with a pasteur pipette (Falcon, 354647). Undissolved tissues or vascular cells were settled, and then a supernatant was taken to measure the cell number and the isolated cells were seeded at 19,000 cells/$cm^2$ in a 35 mm culture dish coated with poly-L-ornithine (sigma, P3655) and fibronectin (sigma, F4759). The cells were cultured using a serum-free $N_2$ medium (growth medium) added with 10 ng/mL bFGF (Invitrogen) in a 5% $CO_2$ incubator, and the culture medium was replaced after 6 hours and after 24 hours. After 2 days, when the cells proliferated twice or more, subculture was performed.

After 3 days of the primary neural progenitor cell culture, a process of subculturing with 0.05% trypsin was repeated twice, and DNA electroporation or transfection was performed before seeding. $2\times10^6$ cells were added with pEGFP-LC3 plasmid at a 1.5 μg DNA ratio and mixed with 82 μl of a nucleofector solution (Lonza, S-06387) and 18 μl of Supplement1 (Lonza, 5-06372) contained in an Amaxa Rat Neuronal Stem Cell Nucleofector Kit (Lonza, VPG-1005), and then plasmid DNA was introduced into the cells using a 4D-Nucleofector X Unit (Lonza, AAF-1001X) electroporator. The introduced cells were seeded on a coverslip located in a 24-well culture dish and cultured for 24 hours in an N2(+bFGF) medium for growth. Thereafter, while the cells were grown in an N2(−FGF) medium for differentiation without the addition of FGF, a 50% medium was replaced every two days to induce neuronal differentiation. After 2 days of differentiation, 0.1 μM rapamycin and 0.1 μM to 0.5 μM HN-1703 were treated.

The number of cell nuclei labeled with DAPI and the number of cells expressing green fluorescence by overlapping LC3-eGFP expression and DAPI labeling were measured. The number of eGFP-LC3 puncta was measured per cell, and the signal intensity of puncta was measured using a confocal laser microscope program. Data analysis was compared between a control group and an experimental group through a one-way analysis of variance (Anova). The statistical significance of the data was set at $p<0.05$.

Results

The autophagy promoting effect of HN-1703 in neurons differentiated by culturing hippocampal neural progenitor cells from rat embryos (E16) was evaluated by performing an LC3-eGFP puncta formation assay. The neural progenitor cells into which an LC3-eGFP recombinant gene was introduced by electroporation were differentiated into neurons, treated with rapamycin and HN-1703 at concentrations of 0.1 μM and 0.5 μM for 12 hours, respectively, and the puncta of LC3-GFP were scanned with a confocal laser microscope (Zeiss, LSM800) to measure the fluorescence intensity of LC3-eGFP and the number of puncta, and the results were illustrated in FIG. 3. Specifically, FIG. 3A illustrates confocal scanning micrographs of LC3-eGFP puncta formation after treated primary cultured hippocampal neurons overexpressing an LC3-eGFP fusion protein with HN-1703, and quantifying the number and fluorescence intensity of LC3-eGFP puncta per cell, and FIG. 3B illustrates a result of LC3-II turnover analysis.

Figure 3A:
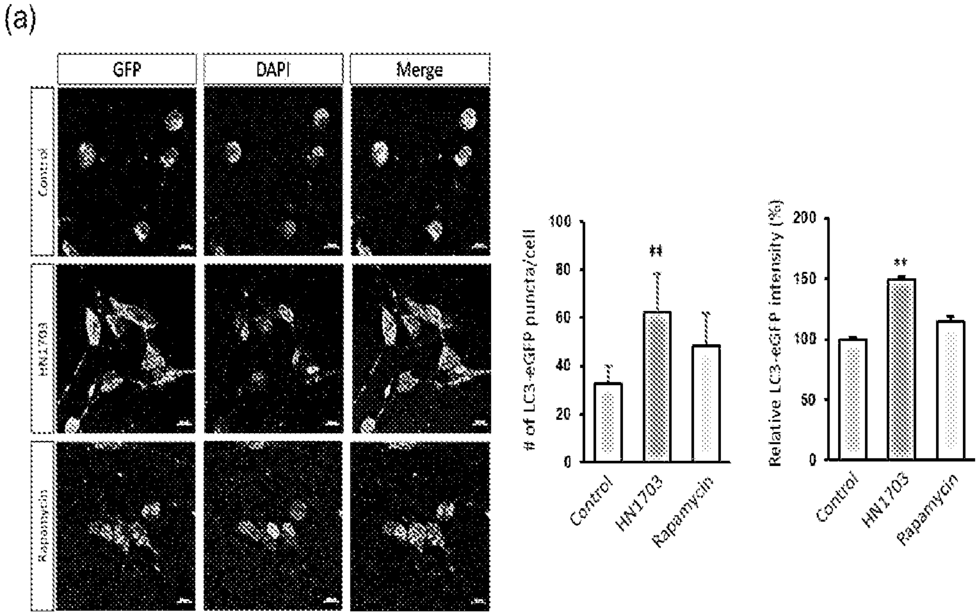
FIG. 3A is a result of illustrating LC3-eGFP staining and the number of puncta and FIG. 3B is a result of LC3 immunoblot analysis showing that a compound of one embodiment of the present invention promotes autophagy more than conventional Rapamycin in primary cultured hippocampal neurons.

Referring to FIG. 3A, it was confirmed that HN-1703 increased the number of LC3-eGFP puncta by 85% or more compared to a control group and increased the signal intensity of puncta by 45% or more compared to the control group. In a parallel experiment, rapamycin only increased the number of LC3-eGFP puncta by 49% and the signal intensity of puncta by 15%, but HN-1703 may promote autophagy more efficiently at a used concentration compared to rapamycin.

Figure 3B:
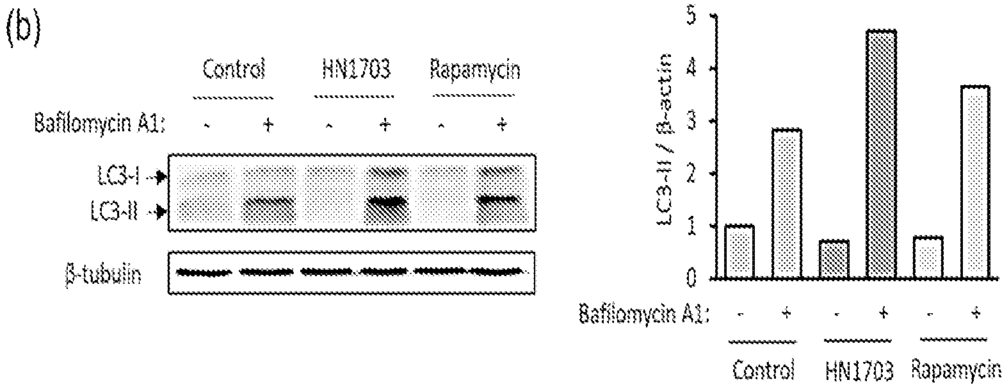

Referring to FIG. 3B, it was confirmed that in primary cultured neurons, HN-1703 significantly increased LC3-II, an autophagy activation marker, up to 36 hours after treating the compound, compared to the control group. In addition, it was confirmed that even in the presence of bafilomycin A1, a lysosome mature inhibitor, HN-1703 significantly increased LC3-II formation compared to the control group, and accordingly, HN-1703 promoted the initial stage of autophagy.

Experimental Example 3. Evaluation of Aβ Accumulation Inhibitory Efficacy

Method

Primary neurons culture was performed from the cerebral cortex of E16 embryos on embryonic day 16 of mice (SD, Orient Bio). Primary neurons culture (cortical neurons culture) was performed from the cerebral cortex of rat (SD, Orient Bio) embryonic 16-day (E16) embryos. The left and right hemispheres of the extracted brain were separated using sterile tweezers under a dissecting microscope, the meninges were peeled off, and then the cerebral cortex region was cut with No. 5 tweezers and collected in a $Ca^{2+}/Mg^{2+}$-free HBSS (Invitrogen), and mixed with an equal amount of 0.25% trypsin in a 15 ml tube and treated in a 37° C. water bath for 10 to 15 minutes. Thereafter, trypsin was inactivated by removing a portion of trypsin, leaving 1 to 2 ml of trypsin, and then adding the same amount of 20% FBS-DMEM. The cells were centrifuged at 700 rpm for 15 minutes to remove a supernatant, added with 2 ml of neurobasal media, and dissolved by slow trituration while changing a pasteur pipette (Falcon, 354647) to a pasteur pipette made with a narrow end. The remaining clumps were filtered by inserting a 40 μm nylon mesh into a 50 ml tube, and the cells remaining on the mesh were washed with 20 ml neurobasal media to obtain additional cells. After measuring the cell number, the isolated cells were seeded on a 35 mm culture dish coated with 50 μg/ml poly-D-Lysine (sigma, P0899) and 1 μg/ml laminin (Invitrogen, 23017-015) at 19,000 cells/$cm^2$. The cells were cultured using neurobasal complete media added with B27 (Gibco, 17504-044) in a 5% $CO_2$ incubator.

Primary cultured cerebral neurons were treated with 0.5 μM or 1 μM Aβ and 0.1 μM or 0.5 μM HN-1703 for 12 or 24 hours, and accumulated Aβ was stained with a 6E10 antibody and autophagy formation was simultaneously double-stained with an LC3 antibody, and cell nuclei were labeled with DAPI.

After removing fully the culture medium, the neurons were washed once with PBS, fixed with 4% PFA in PBS for 15 minutes, and then washed twice with PBS. A coverslip attached with the cells was washed with PBST, added with 0.5% Triton X-100-PBST, and then reacted for 10 minutes. The coverslip was blocked with 2% BSA-PBST or 5% normal donkey serum (Jackson lab, 017-000-121, Normal horse serum: Sigma, H0146) again, the first antibody was added in 2% BSA-PBS and reacted overnight at 4° C., washed with PBST the next day, and then the second antibody was added in PBST and reacted for 1 hour at room temperature, and cell nuclei were stained with DAPI (1 g/mL, Sigma) and placed on a slide glass, and scanned with a confocal laser microscope and photographed. As the first antibody, LC3-II (MBL, PM036) and 6E10 (Biolegend, 803001) were used, and as the second antibody, Alexa 488 (Invitrogen, A21202), Cy3 (Jackson lab, 715-165-151), Alexa 488 (Jackson lab, 711-546-152) and the like were used.

Results

As confirmed in Experimental Example 2 that HN-1703 may effectively promote autophagy, it was evaluated whether HN-1703 may remove Aβ oligomers accumulated in cells. In the rat embryonic (E16) cerebral cortex region, primary cultured cerebral neurons were treated with 0.5 M or 1 μM Aβ and 0.1 μM or 0.5 μM HN-1703 for 12 or 24 hours, and accumulated Aβ was stained with a 6E10 antibody and autophagy formation was simultaneously double-stained with an LC3 antibody and measured, and cell nuclei were labeled with DAPI. After scanning with a confocal laser microscope (Zeiss, LSM800), A3 staining was quantified by a staining signal intensity and LC3 staining was quantified by measuring the area of puncta, and the results were illustrated in FIG. 4.

Figure 4:
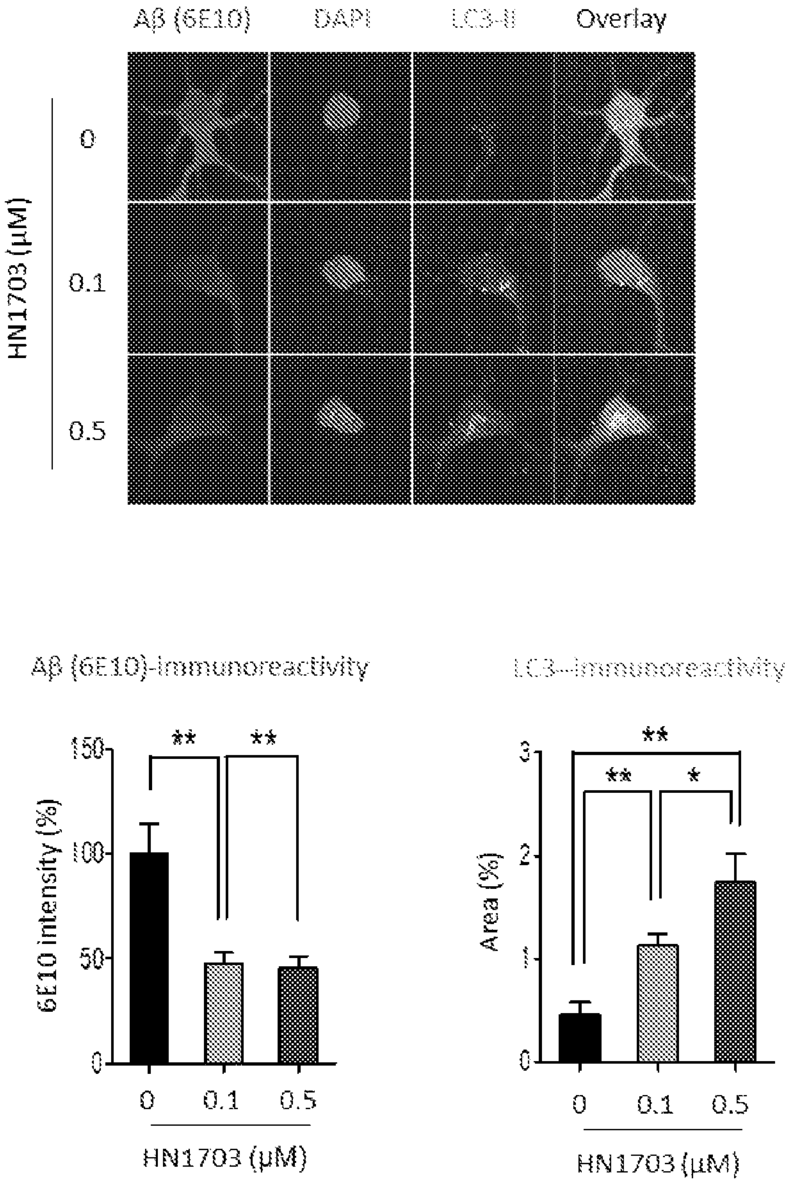
FIG. 4 illustrates results of Aβ staining intensity and LC3 staining area showing that the compound of an embodiment of the present invention removes Aβ accumulated in primary cultured cerebral neurons and simultaneously increases LC3-II puncta.

Referring to FIG. 4, it was confirmed that when treated with HN-1703, the area of LC3 puncta, an autophagy marker, increased in a concentration-dependent manner and increased 4 times or more, and simultaneously, at the same concentration, 50% or more of Aβ accumulated in cells was removed.

Through the experiments, it was confirmed that HN-1703 removed Aβ accumulated in primary cultured cerebral neurons and simultaneously increased LC3-II puncta.

Experimental Example 4. In Vitro Evaluation of Neuron Protective Efficacy Against Aβ Toxicity Method Primary cultured neurons from the cerebral cortex of rat embryos (E16) were treated with 0.5 M or 1 μM Aβ and 0.1 μM or 0.5 μM HN-1703 for 12 or 24 hours. Cell viability was evaluated by measuring the number of cells stained with DAPI.

Results

Aβ has strong toxicity to neurons, and the death of neurons caused by Aβ accumulated in the brain is a major cause of Alzheimer's disease. To evaluate whether HN-1703 for inhibiting the mTOR signaling pathway and promoting autophagy may directly protect neurons from Aβ toxicity, an inhibitory effect of HN-1703 on Aβ-induced apoptosis of primary cultured cerebral neurons was evaluated, and the number of live cells stained with DAPI was quantified and shown in FIGS. 5A and 5B.

Figure 5A:
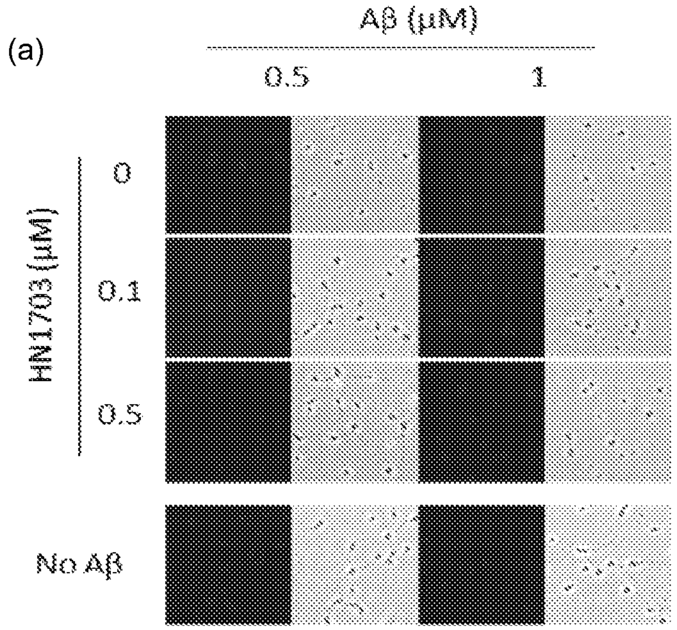
FIGS. 5A and 5B are analysis results of showing that the compound of an embodiment of the present invention protects primary cultured hippocampal neurons from Aβ cytotoxicity to promote cell survival, through viability by counting the cell number.
Figure 5B:
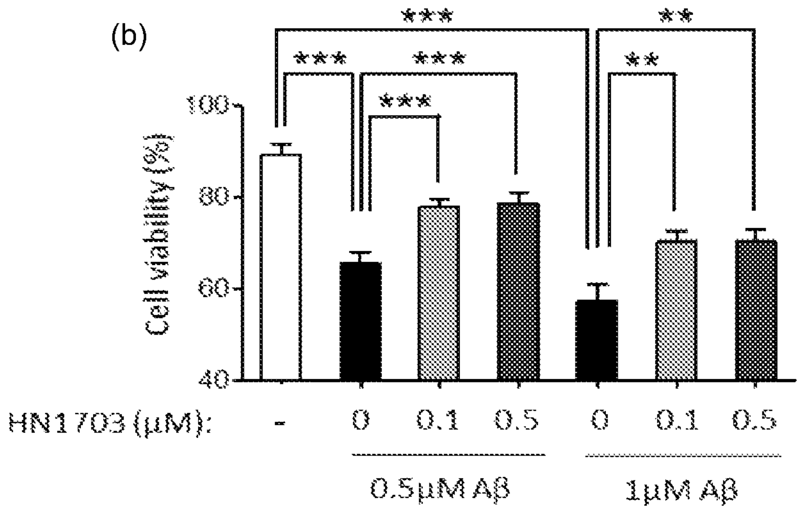

Referring to FIGS. 5A and 5B, it was confirmed that the cell viability was reduced by 50% or more by Aβ, and the viability was significantly increased by HN-1703 treatment.

Evaluation of In Vivo Efficacy of HN-1703 on 5xFAD Transgenic Mice, as Dementia Animal Model Purpose of Experiment This experiment was performed to 1) confirm an effect of HN-1703 on Alzheimer's disease-related disease symptoms, specifically, i) an effect on the accumulation of senile plaques in the brain, ii) an effect on tau-phosphorylation in the brain, and iii) an effect on inflammatory responses in the brain, 2) confirm a mechanism of action, specifically, i) an effect on autophagy in the brain, and ii) an effect on neurogenesis in the hippocampus, and 3) evaluate the efficacy of improving memory and cognitive function.

Method

HN-1703 Administration to 5xFAD Mice

5xFAD animals were administered with HN-1703 at three doses for 14 days to male heterozygotes aged 6 months (all born within 3 days). The behaviors of mice were measured in a dark cycle in which the mice were active while alternating light and dark in a 12-hour cycle in a breeding room chamber, and the mice were freely accessible to food and water and bred in compliance with experimental animal ethical guidelines of Kyung Hee University. In each group, the HN-1703 was intraperitoneally injected at the same time once a day in a volume of 100 μl to 12 mice in a normal group (wild type littermate), 9 5xFAD mice in a vehicle (DMSO administration), 8 5xFAD mice in a 5 mg/kg administered group, 9 5xFAD mice in a 10 mg/kg administered group, and 9 5xFAD mice in a 20 mg/kg administered group. Cognitive function was measured after habituation for 10 minutes every day for 5 days until the mice were placed on the palm and then did not escape from the palm for 2 minutes to get used to the hand and smell of a behavioral measurer. In a behavioral measurement room, humidity (40 to 60%) and temperature (22 to 26° C.) were maintained, and reflected light was maintained to avoid sound and light effects. Behavioral measures were measured in Y-maze, Morris Water Maze, and Passive Avoidance test for 18 days in sequence.

Y-Maze Task

When a mouse was placed in a Y-maze and the mouse explored the maze, it was measured whether the mouse selected a new maze alternately from the center or selected the same maze again after forgetting the maze, and the number of alterations was calculated as a percentage %. In the detailed measurement method, by referring to the content disclosed in Heo H et al. (J Ethnopharmacol, 2009), the spatial memory and short-term memory of the mouse were tested. In the Y-maze, the mouse entering each arm was photographed for 8, 10, and 20 minutes, and the probability of success (%) was calculated by dividing the number of times entering each of three different arms by the total number of times entering the arm—2. All results were statistically processed using an ANOVA test.

Passive Avoidance Test

A passive avoidance test was performed as described in Heo et al. in the order following the Y-maze task (J Ethnopharmacol, 2009). As a result of the avoidance action by strong light, while the mouse trained a practice of avoiding from a bright room to a dark room 3 times a day for 4 days, the mouse was accustomed to the environment, and when the mouse avoided within 30 seconds (acquisition time), an electric foot shock (0.5 mA, based on 30 g) was applied to the mouse for 3 seconds in a dark room at the same time the next day. After exactly 24 hours, the mouse was placed in a bright room again, and the memory retention time required for the avoidance response by light, that is, to move from a bright room to a dark room was measured for 720 seconds (confinement experiment), and latency time was measured for each group.

Morris Water Maze Test

A Morris water maze test designed by Richard Morris to test spatial memory was performed on a round and rust-free pool with a white inner-surface (diameter 120 cm; height 60 cm). For the pool, a water tank containing water (maintained at 25.0±1.0° C.) at a depth of 50 cm was equally divided into 4 parts, and a platform (approximately 12 cm in diameter) was located in the middle of one section at a depth of 3 mm from the water surface. On the first day, the mice were trained in free swimming for 1 minute without a platform foothold, and from the second day, while the mice were trained for 1 minute to find the platform using a spatial clue above the water tank by dissolving dye in water so as not to see the foothold, 6 mice or more were set to a group and put into a quadrant once after taking a sufficient rest, and measured by a video camera. A training test was performed to find the foothold of the water tank 4 times a day for 4 days, and in the final experiment on last day 6, after removing the foothold of the water tank, the time taken while the experimental animals stayed at the foothold was measured (probe trial). The captured video pictures were analyzed with a video tracking system (Ethovision water maze program, Noldus Information Technology, Wageningen, Netherlands). The analyzed information included the time taken for swimming in a target quadrant and the number of times for crossing a virtual platform to find the removed platform.

Immunohistochemical Staining

A brain slice immunostaining method was modified and used as described in Heo H et al. (J Ethnopharmacol, 2009). Mice were transcardially perfused with 4% PFA. After being immersed and fixed in 4% PFA for 4 hours, the brain tissue was unfrozen in 30% sucrose, frozen in an optimal cutting temperature (OCT) mixture, and stored at −80° C. Brain tissue slices were sectioned in a coronal direction at a thickness of 35 μm. The brain tissue slices were immersed in a storage solution (30% glycerol, 30% ethylene glycol, PBS) and stored at 4° C. The stored brain slices were permeabilized in 0.5% Triton X-100 for 20 minutes and shaken in 2 N HCl for 30 minutes at 37° C. Then, the brain slices were blocked in a free-floating state for 2 hours in 15% standard serum, 3% bovine serum albumin (BSA, bio-WORLD, Dublin, OH, USA) and 0.1% Triton X-100.

The slices were shaken with a first antibody for 16 hours at 4° C. Thereafter, a second antibody complementary to the first antibody was attached at room temperature (22±1° C.) for 45 minutes. Then, the nuclei were washed with physiological saline (PBS) containing 1 μg/ml PI (propidiumiodide, Sigma) or DAPI (1:4000), and then placed on a slide glass and sealed using an aqueous mount, and observed under a confocal scanning microscope for tissue observation (LSM 810 Carl Zeiss, Oberkochen, Germany).

The first antibody used antibodies such as LC3-II (MBL, PM036), MAP2 (sigma, m4403) [for LC3/MAP2 double staining], 6E10 (biolegend, 803001) [for LC3/6E10; ICC double staining], GFAP (abcam, ab53554) [for LC3/GFAP double staining], Iba-1 (wako, 011-27991) [for LC3/IBA1 double staining], Iba-1 (Wako, 019-19741) [for ThioS/Iba1/PI triple staining], Sox2 (R&D system, MAB2018) [for SOX2/DCX/NeuN triple staining], DCX (Santa Cruz, sc8066) [for SOX2/DCX/NeuN triple staining], AT8 (Invitrogen, MN1020) [for AT8/MAP2 double staining], MAP2 (abcam, ab32454) [for AT8/MAP2 double staining], NeuN (Millipore, MAB377B), Tuj1 (Sigma, T8660), Nestin (Millipore, MAB353), GFAP (Chemicon), and the like, and the second antibody used Alexa 488, Cy3, Alexa 488 (Invitrogen, A21202), Cy3 (Jackson lab, 715-165-151), and Alexa 488 (Jackson lab, 711-546-152).

Experimental Example 5. Evaluation of Memory and Cognitive Function Improvement in 5xFAD Mice FIG. 6 is analysis results of a Y-maze task, a passive avoidance test, and a Morris water maze test showing that HN-1703 has an effect of restoring a cognitive function that has been reduced when administered to a dementia animal model, 5xFAD transgenic mice.

Figure 6:
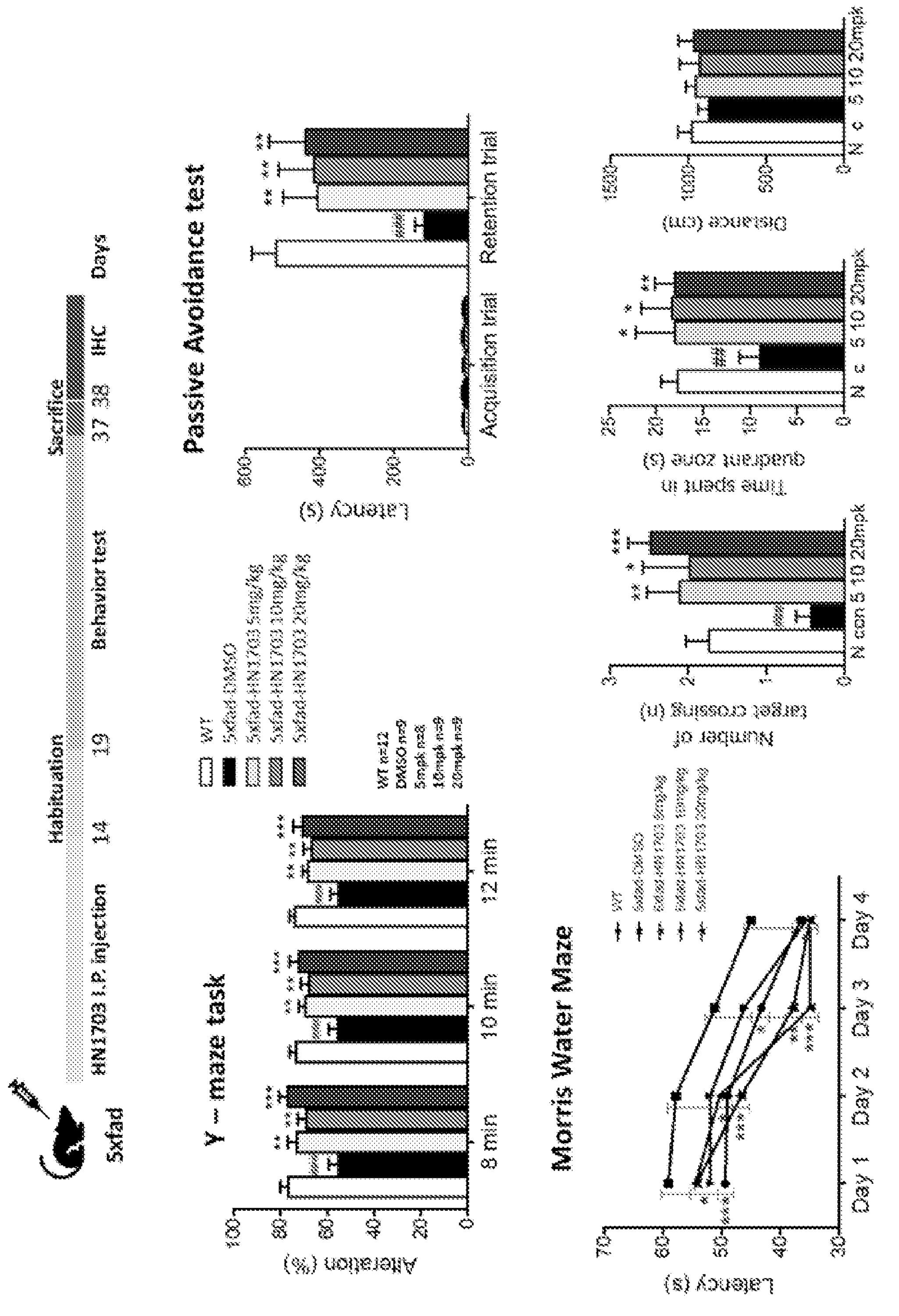
FIG. 6 is analysis results of a Y-maze task, a passive avoidance test, and a Morris water maze test showing that the compound of an embodiment of the present invention has an effect of restoring a cognitive function that has been reduced when administered to a dementia animal model, 5xFAD transgenic mice.

Referring to FIG. 6, in the Y-maze task, 5xFAD mice (5xFAD-DMSO) to which only DMSO was administered showed alterations of about 55.6% to 56% at 8, 10, and 12 minutes of measurement ($P<0.001$ compared to a normal group). However, alterations of 68% to 73% in a 5 mg/kg administered group administered with HN-1703 to 5xFAD, 67% to 69.5% in a 10 mg/kg administered group, and 71.3% to 77.4% in a 20 mg/kg administered group were shown (significant $P<0.001$ to 0.01), which was confirmed to be recovered to a value similar to that of the normal group (72.0% to 75.5%).

In the passive avoidance test, it was confirmed that in a 5xFAD-DMSO group (about 122.3 seconds), a latency time was reduced by 76.5% compared to a normal group (about 519.9 seconds), but in mice administered with 5 mg/kg, 10 mg/kg, and 20 mg/kg of HIN-1703, the latency time was significantly recovered to 418.4 seconds to 447.3 seconds.

In the water maze test, it was confirmed that in the 5xFAD-DMSO group, the latency time increased by about 10 seconds compared to normal mice throughout a training period, whereas in groups administered with 5 mg/kg, 10 mg/kg, and 20 mg/kg of HN-1703, on the first day, it took longer to find a foothold than the normal group, but a learning speed was faster than the normal group, and after 4 days of training, the latency time decreased to about 35 seconds, which was similar to the normal group. A swimming distance was similar in all experimental groups, but the swimming time in a target quadrant (quadrant 1) was 9 seconds in the 5xFAD-DMSO group, which was 54% of 16.6 seconds in the normal group, and 17.5 to 18.4 seconds in the HN-1703-administered group, which was longer than the normal group. The number of times passing through the place where the target was located was 0.44 times in the 5xFAD-DMSO group, which was 30% of 1.47 times in the normal group, and increased to 2 to 2.4 times in the HN-1703-administered group in a concentration-dependent manner. Therefore, it was confirmed that the spatial perception which has been reduced in 5xFAD mice compared to the normal group was restored to the level of the normal group by administration of HN-1703.

Experimental Example 6. Evaluation of Senile Plaques Removal Efficacy in 5xFAD Mouse Brain Brain slices segmented in a coronal direction were selected from the front to the back of the brain by one slice every 5 slices, and 5 to 11 slices for each animal's brain were co-stained with thioflavin-S and DAPI. The hippocampal dentate gyrus, and the entorhinal cortex, the subiculum, and the temporal lobe of the cerebral cortex, where many senile plaques and neurofibrillary tangles (NFTs) are deposited, were observed with a confocal laser microscope.

Figure 7:
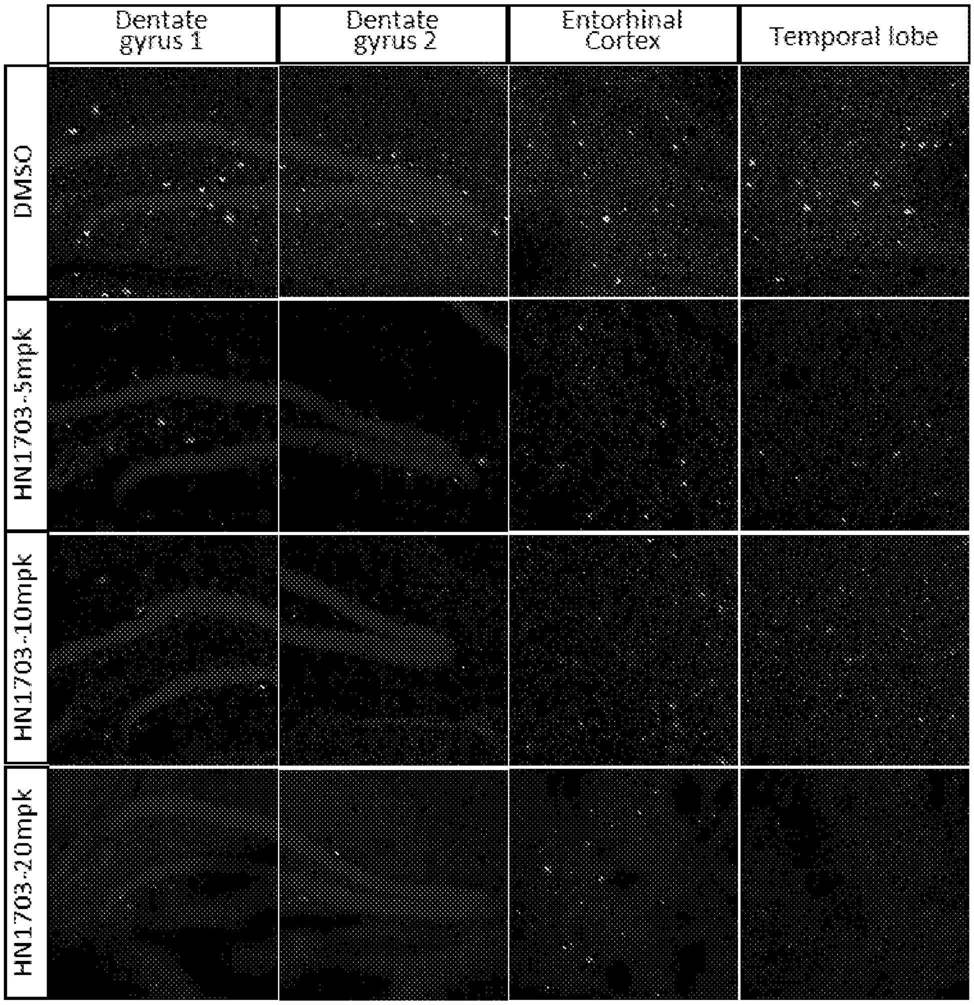
FIG. 7 is confocal scanning micrographs of the hippocampal dentate gyrus, the cerebral entorhinal cortex, and the lateral temporal lobe, after the senile plaques of the brain slice are stained with Thioflavin-S.
Figure 8:
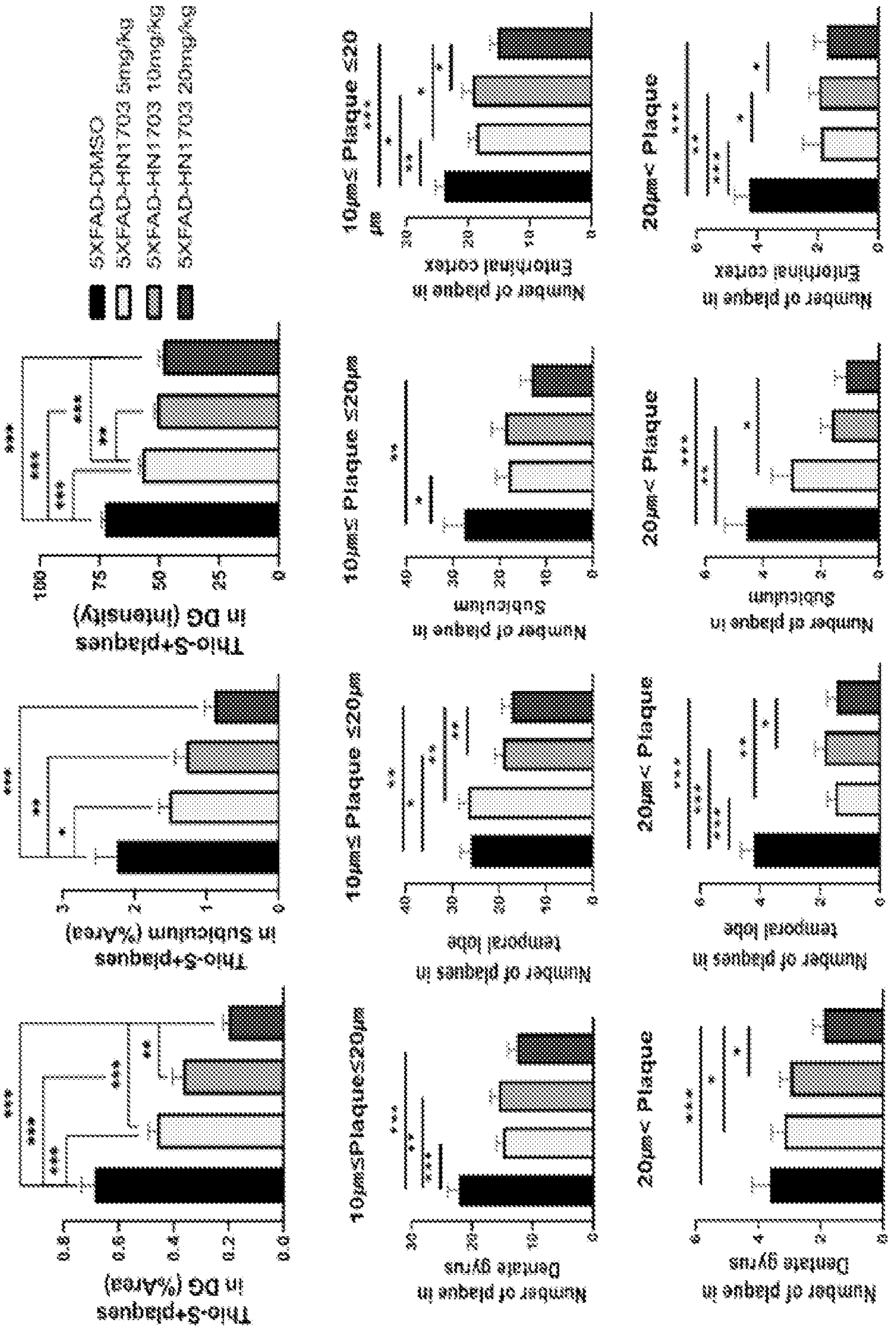
FIG. 8 illustrates quantifying the total area and staining intensity of senile plaques stained with Thioflavin-S in the hippocampal dentate gyrus and subiculum, where senile plaques are found most often, and dividing the senile plaques into sizes of 10 μm or more, 20 μm or less, and 20 μm or more depending on a size, and counting the number of senile plaques by a brain region.

FIG. 7 is confocal scanning micrographs of the hippocampal dentate gyrus, and the entorhinal cortex and temporal lobe of the cerebral cortex, after staining senile plaques by treating the brain slice with Thioflavin-S, and FIG. 8 illustrates quantifying the entire area and staining intensity of the senile plaques stained with Thioflavin-S.

Referring to FIG. 7, it was confirmed that the senile plaques stained with Thioflavin-S were most frequently found in the hippocampal dentate gyrus, the entorhinal cortex, and the temporal lobe in the 5xFAD-DMSO group, reduced in a dose-dependent manner by administration of HN-1703 at the doses from 5 to 20 mg/kg, and reduced by 70% or more compared to the 5xFAD-DMSO group in the dentate gyrus of 5xFAD mice administered with HN-1703 at 20 mg/kg.

Referring to FIG. 8, it was confirmed that in the HN-1703-administered group, both the entire area and the staining intensity of senile plaques decreased in a dose-dependent manner compared to the 5xFAD-DMSO control group, and in all brain regions to be tested, the number of senile plaques having sizes of 10 to 20 μm and 20 μm or more decreased in a dose-dependent manner in the HN-1703-administered group compared to the 5xFAD-DMSO control group.

As a result of the experiment, it was confirmed that HN-1703 reduced the senile plaques when administered to 5xFAD transgenic mice in a dementia animal model.

Experimental Example 7. Evaluation of NFT Removal Efficacy in 5xFAD Mouse Brain An AT8 antibody stained a hyperphosphorylated Tau protein. Accordingly, NTF formed in the hippocampus and cerebral cortex of the 5xFAD mouse brain may be observed by immunostaining using the AT8 antibody. Brain slices were triple-stained with an AT8 antibody, MAP2 antibody as a neuronal marker, and DAPI staining cell nuclei.

Figure 9:
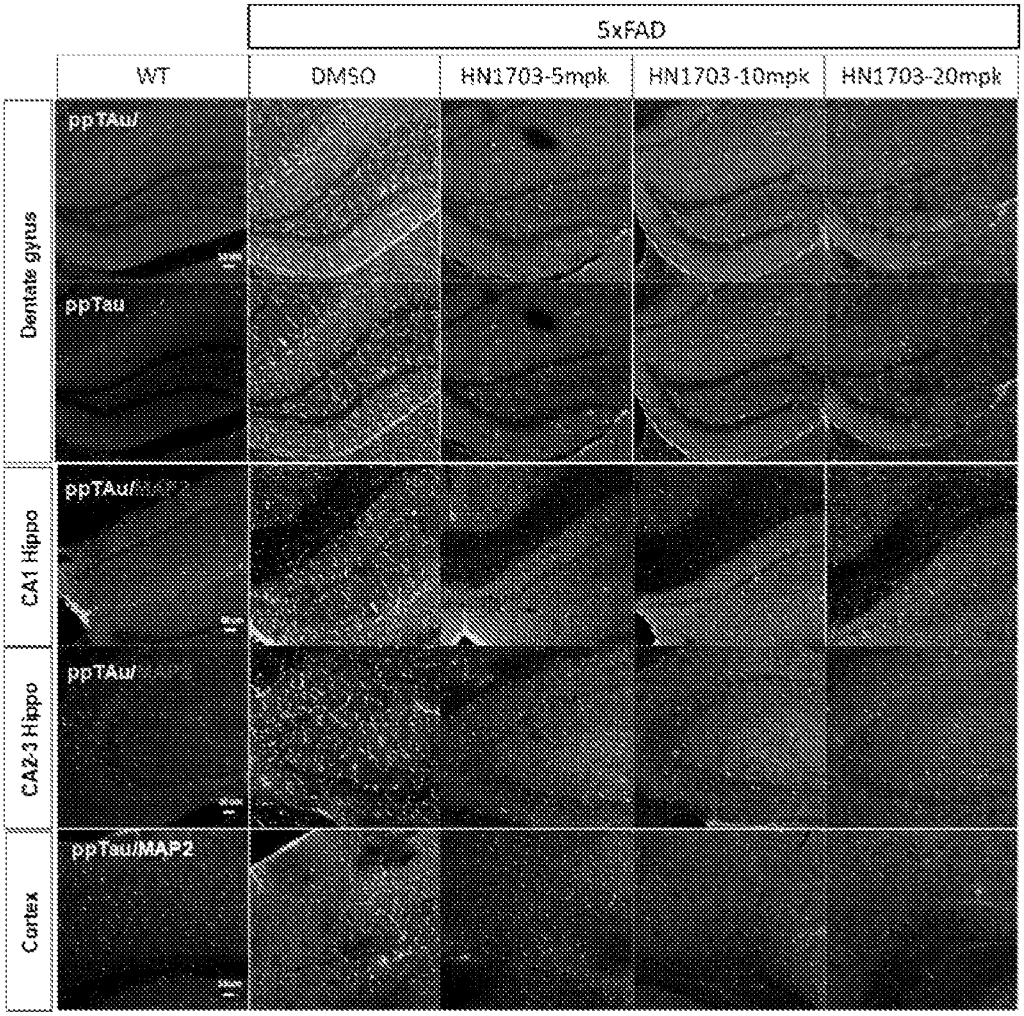
FIG. 9 is confocal scanning micrographs of the dentate gyrus, CA1, and CA3 regions of the hippocampus, and a cerebral cortex region after a double staining of brain slices with an AT8 antibody that recognizes hyperphosphorylated Tau-NFT and an MAP2 antibody that mainly stains dendrites of neurons.
Figure 10:
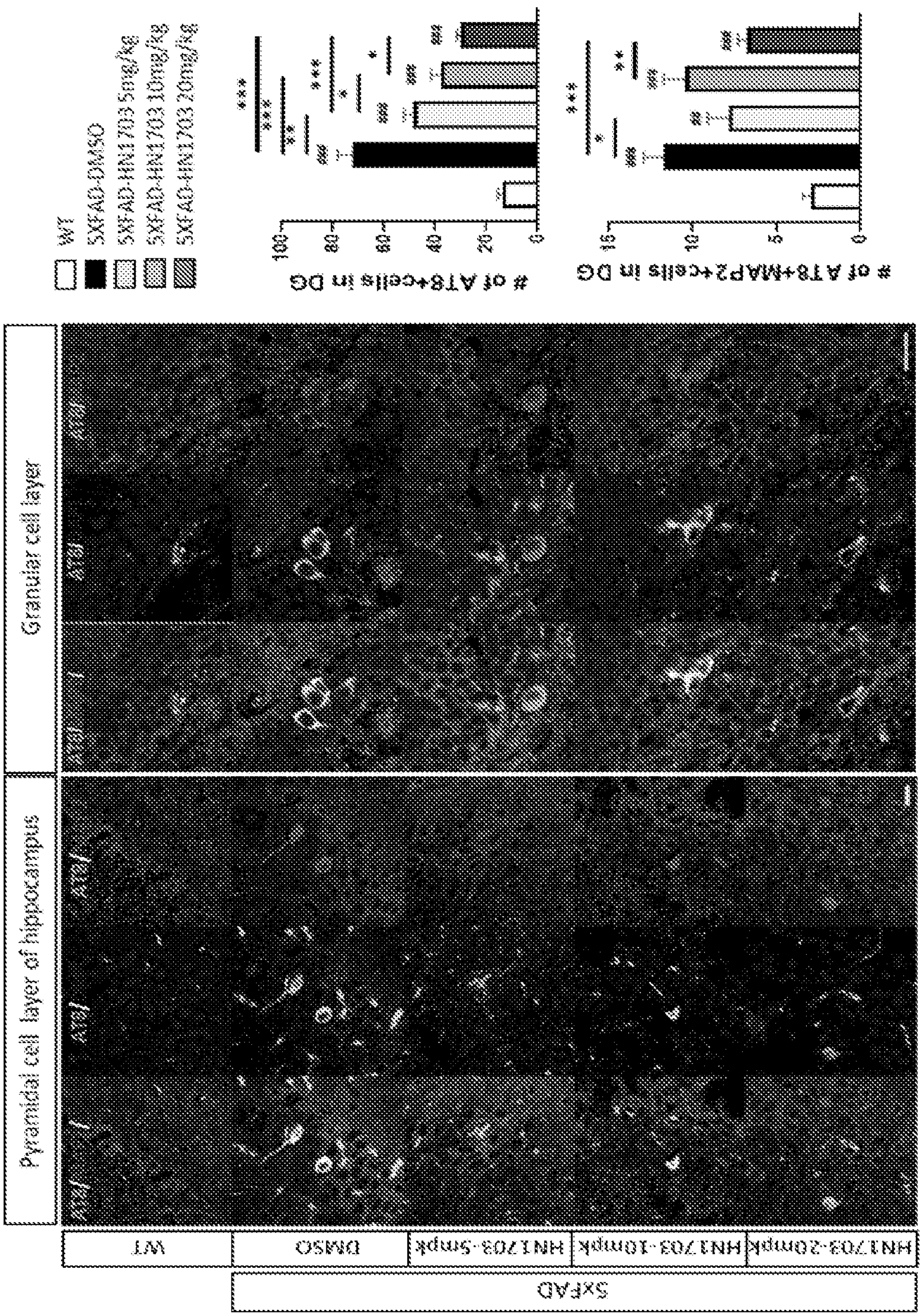
FIG. 10 shows confocal scanning micrographs in a high magnification after double staining with an MAP2 antibody and an AT8 antibody and quantifying the number of AT8-stained (AT8+) cells and the number of AT8-stained neurons (MAP2+) observed in the dentate gyrus.

FIG. 9 is confocal scanning micrographs of the dentate gyrus, CA1, and CA3 regions of the hippocampus and the cerebral cortex region after a double staining of brain slices with an AT8 antibody that recognizes hyperphosphorylated Tau-NFT and an MAP2 antibody that mainly stains dendrites of neurons, and FIG. 10 shows confocal scanning micrographs in a high magnification after double staining with an MAP2 antibody and an AT8 antibody and quantifying the number of AT8+ cells and the number of AT8+/MAP2+ cells observed in the dentate gyrus.

Referring to FIG. 9, in the brain of 5xFAD mice, NFTs were observed most in the dentate gyrus, observed second in the CA1 and CA2 regions of the hippocampus, and observed relatively small in the cerebral cortex. It was confirmed that the NFT was decreased in a dose-dependent manner by administration of HN-1703 at the doses from 5 to 20 mg/kg in all three brain regions to be examined. In the dentate gyrus of the 5xFAD-administered group administered with HN-1703 at 20 mg/kg, NFTs were decreased by 70% or more compared to the 5xFAD-DMSO group.

Referring to FIG. 10, it was confirmed that NFT was mainly double-stained with neurons, and it was confirmed that the number of neurons stained with NFT also decreased in a dose-dependent manner by administration of HN-1703.

As the experiment result, it was confirmed that HN-1703 reduced the NFTs when administered to 5xFAD transgenic mice in the dementia animal model.

Experimental Example 8. Evaluation of Neuroinflammation Inhibitory Efficacy in 5xFAD Mice Microglia were immune cells responsible for the inflammatory responses in the brain. Activated microglia significantly increased in 5xFAD mice compared to a normal group. Since the activated microglia were stained with Iba-1, brain slices were stained with Iba-1 to evaluate an effect of administration of NH-1703 on the neuroinflammation.

Figure 11:
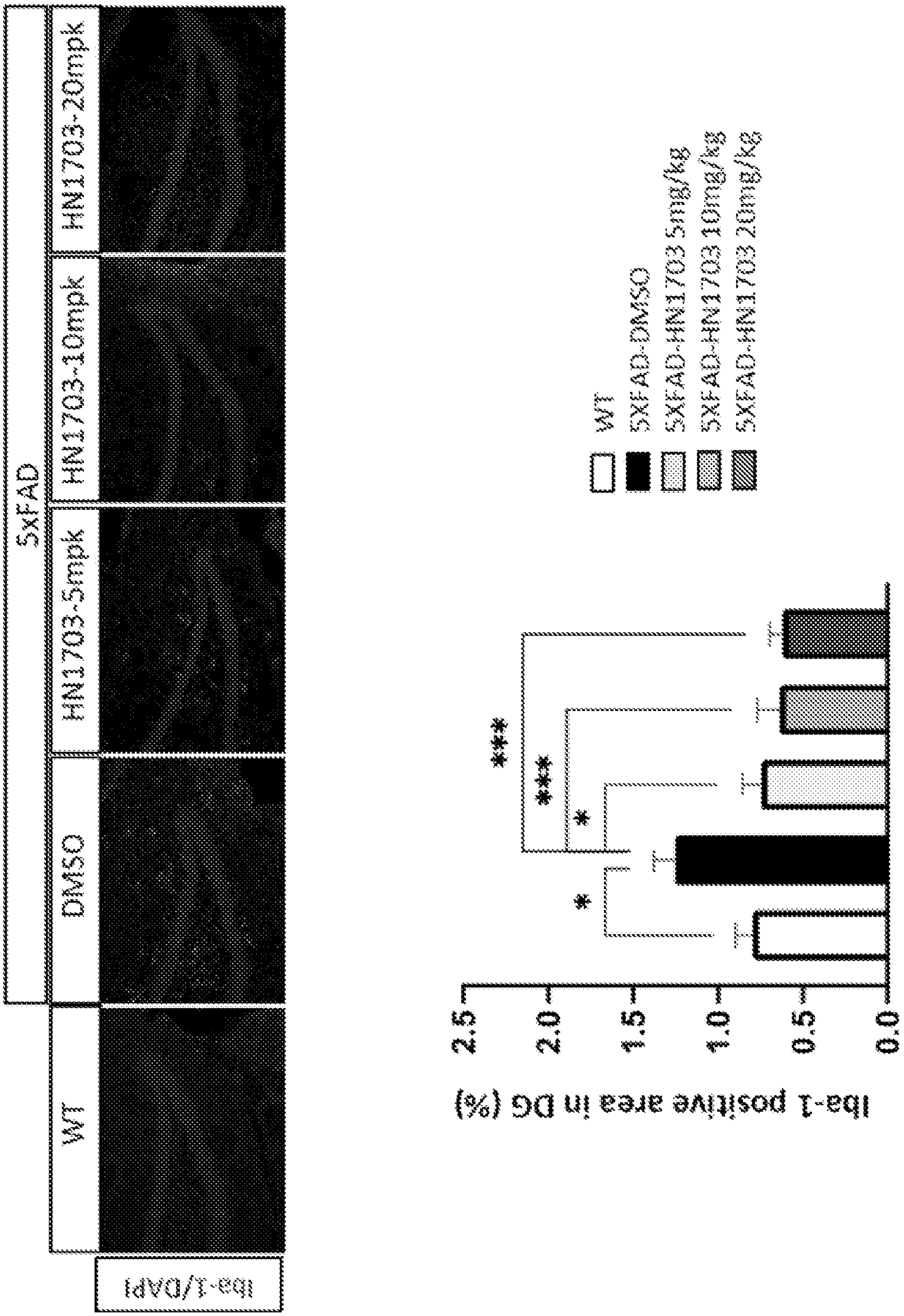
FIG. 11 shows confocal scanning micrographs of the hippocampal dentate gyrus region double-stained with an Iba-1 antibody staining activated microglia, and DAPI staining cell nuclei, and quantifying Iba-1-stained areas.

FIG. 11 shows confocal scanning micrographs of the dentate gyrus region of the hippocampus double-stained with an Iba-1 antibody staining activated microglia and DAPI staining cell nuclei, and Iba-1+ areas.

Referring to FIG. 11, it was confirmed that Iba-1 staining in the HN-1703-administered group was significantly reduced compared to a 5xFAD-DMSO control group.

As the experiment result, it was confirmed that HN-1703 suppressed the neuroinflammation when administered to 5xFAD transgenic mice in a dementia animal model.

Experimental Example 9. Evaluation of Autophagy Indicators in 5xFAD Mice

When HN-1703 was administered to 5xFAD transgenic mice, senile plaques and NFTs were significantly reduced, and autophagy activation indicators were examined. When PS1 was KO, lysosome acidification was weakened and autophagy was inhibited (Lee et al. (2010) Cell 141: 1146-1158), and in 5xFAD mice with mutations in PS1, the generation of autophagy was somewhat attenuated and may be activated in the presence of endogenous WT PS1. In other words, there were example in which cellular conditions that inhibit mTOR, such as lack of amino acids, or suppression of inflammation activated autophagy, and treatment with a cAMP or β-adrenergic agonist restored lysosomal acidification in PS1 mutant cells (Coffey et al. (2014) Neuroscience 263: 111-124). To examine the association between the significant reduction in senile plaques and NFT and autophagy activation, brain slices were double-stained with an LC3 antibody as an autophagy activation indicator and a GFAP antibody labeling astrocytes.

Figure 12:
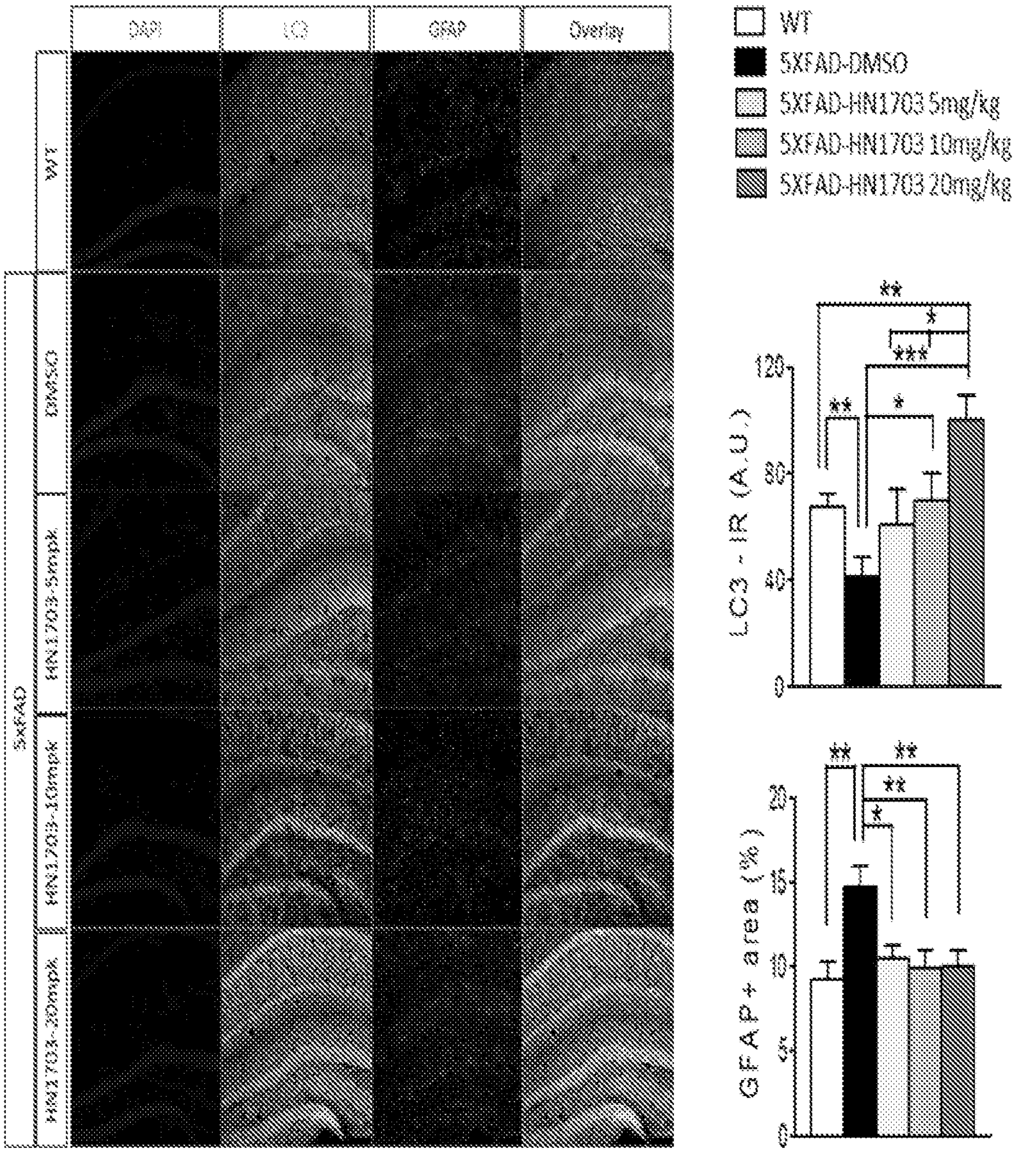
FIG. 12 shows confocal scanning micrographs of the hippocampal dentate gyrus region after triple-staining with an LC3 antibody as an autophagy marker, a GFAP antibody labeling astrocytes, and DAPI staining cell nuclei, and quantifying the number of LC3-stained cells and GFAP-stained areas.
Figure 13:
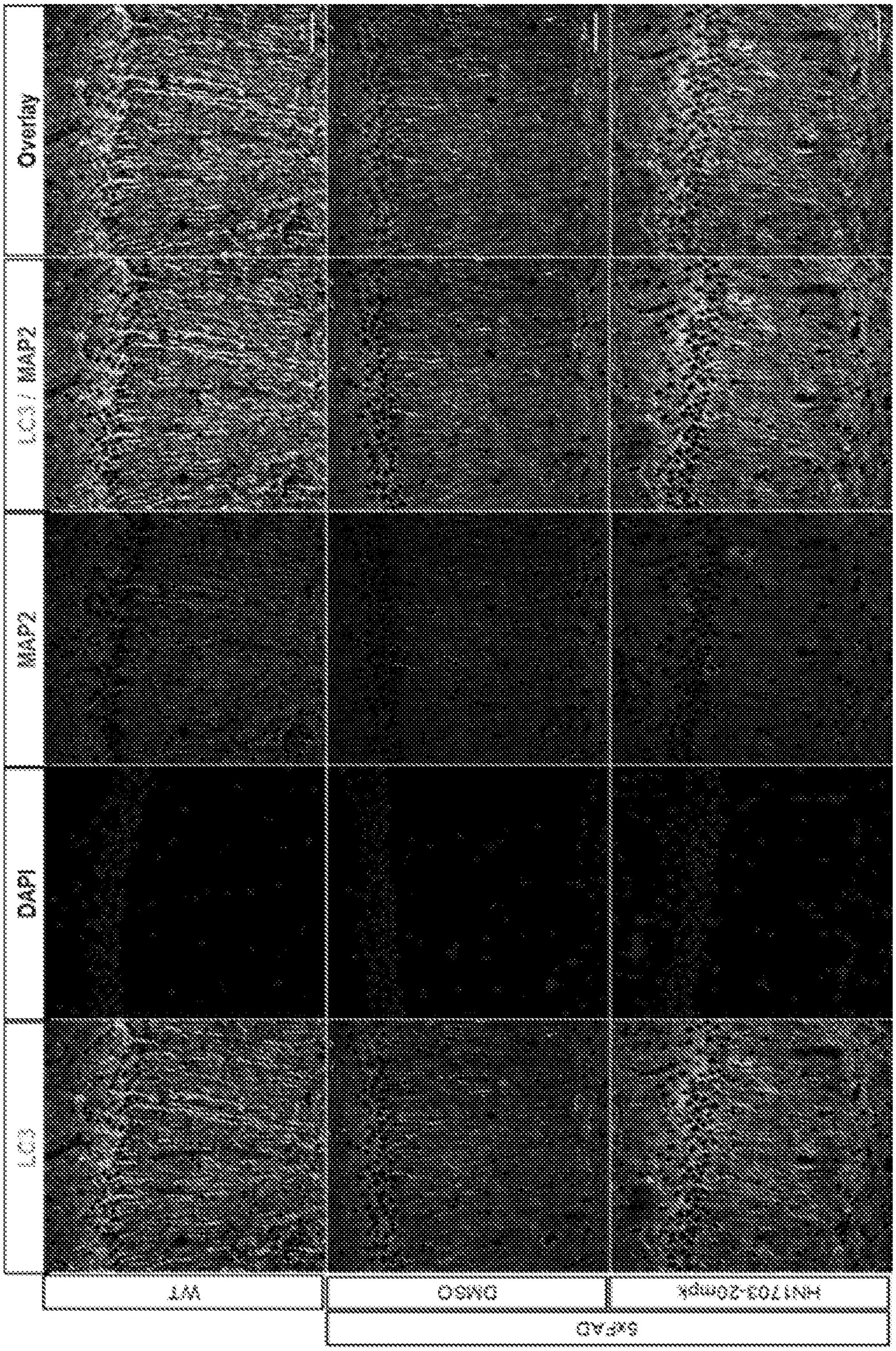
FIG. 13 is confocal scanning micrographs of hippocampal pyramidal cells by double staining with an MAP2 antibody as a neuron marker and an LC3 antibody.
Figure 14:
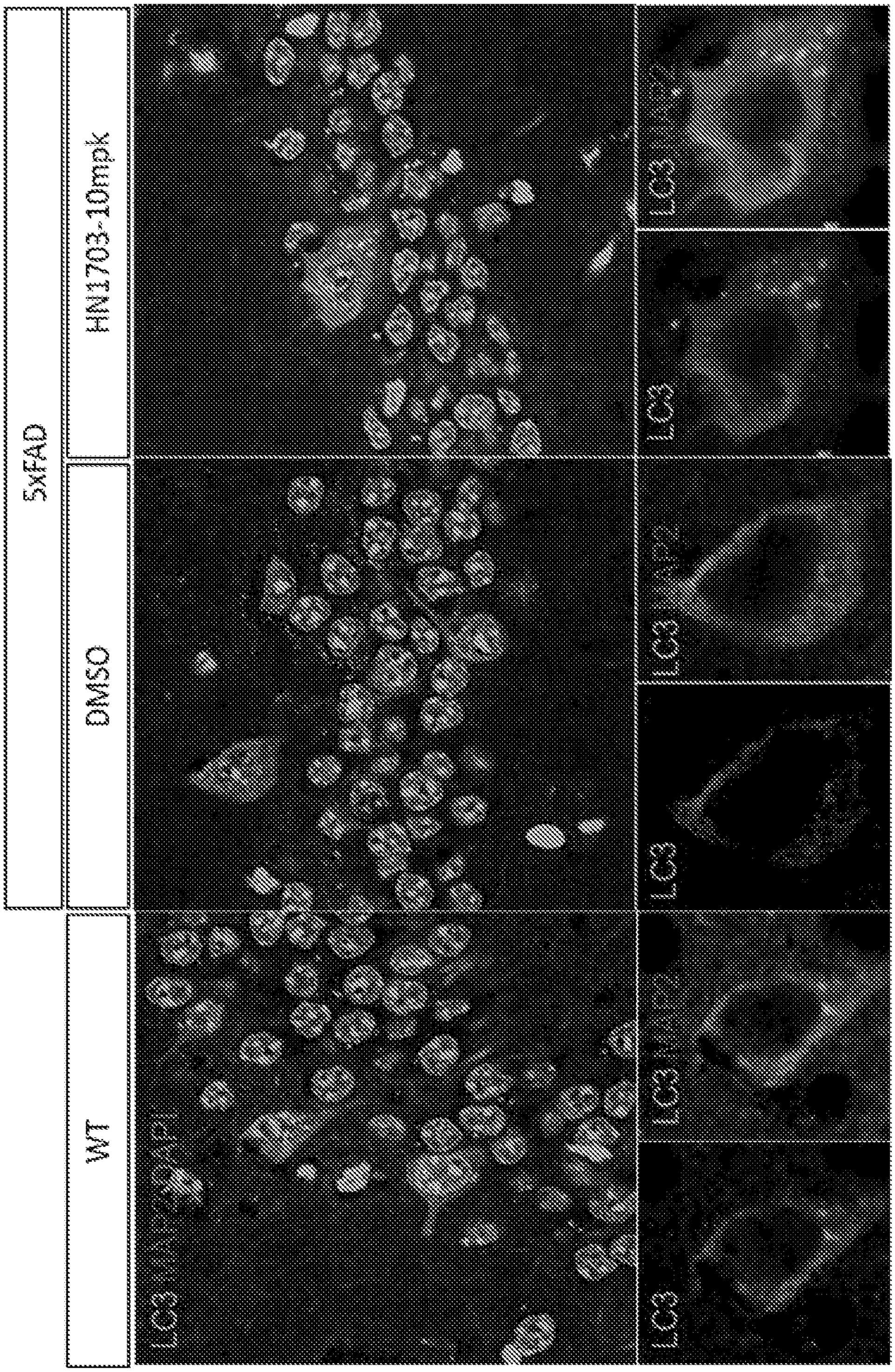
FIG. 14 is high-magnification confocal scanning micrographs of the granule cell layer of the hippocampal dentate gyrus by double staining with an MAP2 antibody and an LC3 antibody.
Figure 15:
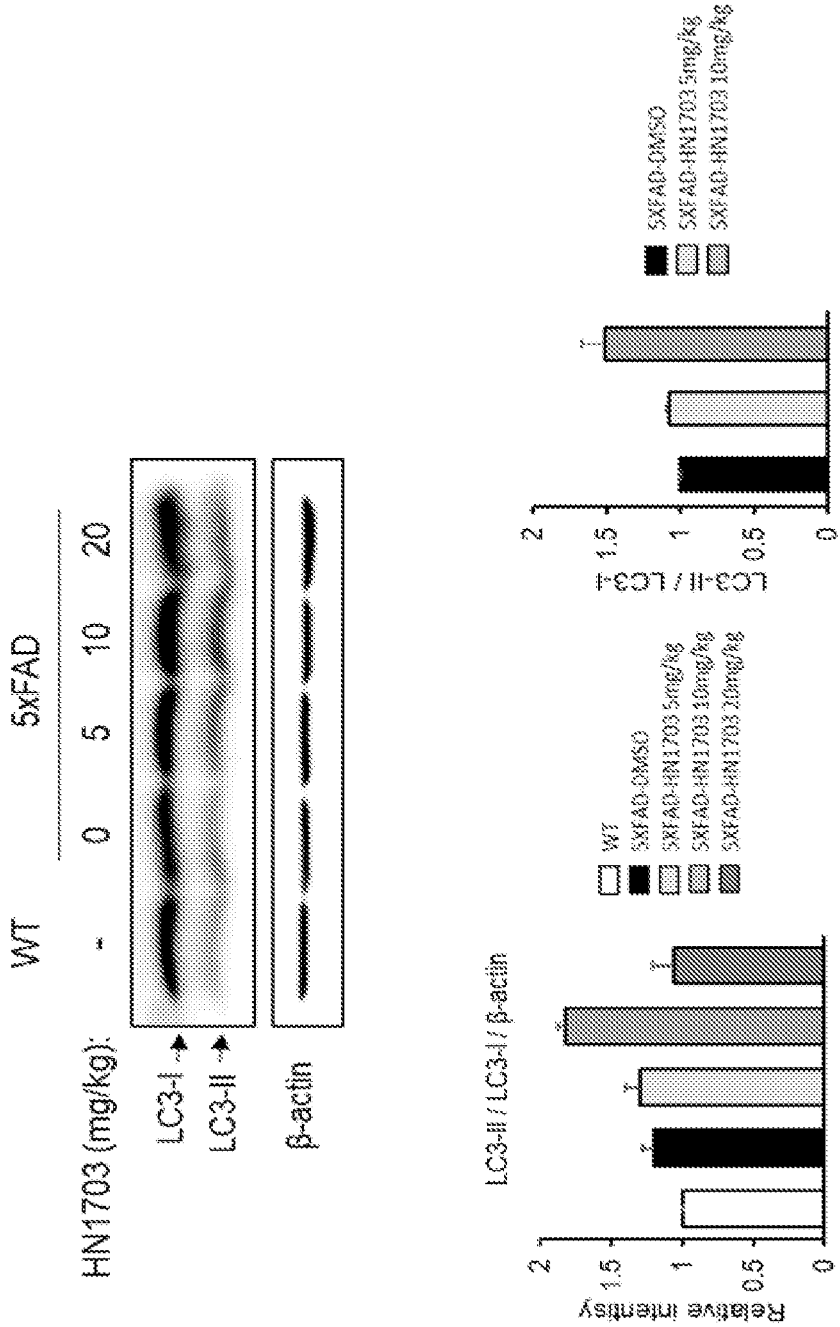
FIG. 15 illustrates a result of immunoblot analysis of protein extracts obtained by extracting the brain and measuring LC3-II formation and a formation ratio of LC3-II to LC3-I.

FIG. 12 shows confocal scanning micrographs of the hippocampal dentate gyrus region after triple-staining with an LC3 antibody as an autophagy marker, a GFAP antibody labeling astrocytes, and DAPI staining cell nuclei, and quantifying the number of LC3-stained cells and GFAP-stained cells, FIG. 13 is confocal scanning micrographs of hippocampal pyramidal cells by double staining with an MAP2 antibody as a neuron marker and an LC3 antibody, FIG. 14 is high-magnification confocal scanning micrographs of the granule cell layer of the hippocampal dentate gyrus by double staining with an MAP2 antibody and an LC3 antibody, and FIG. 15 illustrates a result of immunoblot analysis of a brain extract obtained from the extracted brain and measuring LC3-II formation.

Referring to FIG. 12, it was confirmed that LC3-II staining in the HN-1703-administered group was increased in a dose-dependent manner compared to a 5xFAD-DMSO control group. In a 5 mg/kg to 10 mg/kg HN-1703-administered group, LC3-II was stained at the level of a WT normal group, and in a 20 mg/kg HN-1703-administered group, LC3-II was increased 2.5 times compared to the 5xFAD-DMSO control group and 1.4 times compared to the WT normal group. In the HN-1703-administered group, LC3-II was stained in the hippocampal pyramidal cells and the soma and axon of the granule cells of the dentate gyrus, and it was confirmed that astrocytes stained with the GFAP antibody were significantly increased in the 5xFAD-DMSO group compared to the WT normal group, and decreased to a normal level by administration of HN-1703. There were not many cells double-stained with the GFAP antibody and the LC3 antibody.

Referring to FIG. 13, as a result of double-staining WT brain slices with an MAP2 antibody and an LC3 antibody, LC3-II staining was observed in the axon as well as the soma of the hippocampal pyramidal neuron. The LC3-II staining in the axon of the hippocampal pyramidal neuron was significantly reduced in the 5xFAD-DMSO control group compared to the WT normal group, but recovered to the level of the WT normal group in the 20 mg/kg HN-1703-administered group. From this result, it was confirmed that autophagy was activated in hippocampal pyramidal neurons by administration of HN-1703 in 5xFAD mice.

Referring to FIG. 14, autophagic vacuoles may be observed near the nuclei of large neurons in the subgranular cell layer of the hippocampus in high-magnification photographs, and in the HN-1703-administered group, it was observed that these autophagic vacuoles were significantly increased.

Referring to FIG. 15, as a result of analyzing the brains extracted from WT normal mice, 5xFAD mice, and 5xFAD mice administered with HN-1703 by immunoblot, it was confirmed that the ratio of the autophagy activation marker LC3-II/LC3-I was increased by administration of HN-1703.

Experimental Example 10. Evaluation of Autophagy Activation in Neurons and Microglia in 5xFAD Mice In order to examine cell types in which autophagy is activated, the MAP2 antibody, the GFAP antibody, and the Iba-1 antibody were double-stained with the LC3 antibody, respectively.

Figure 16:
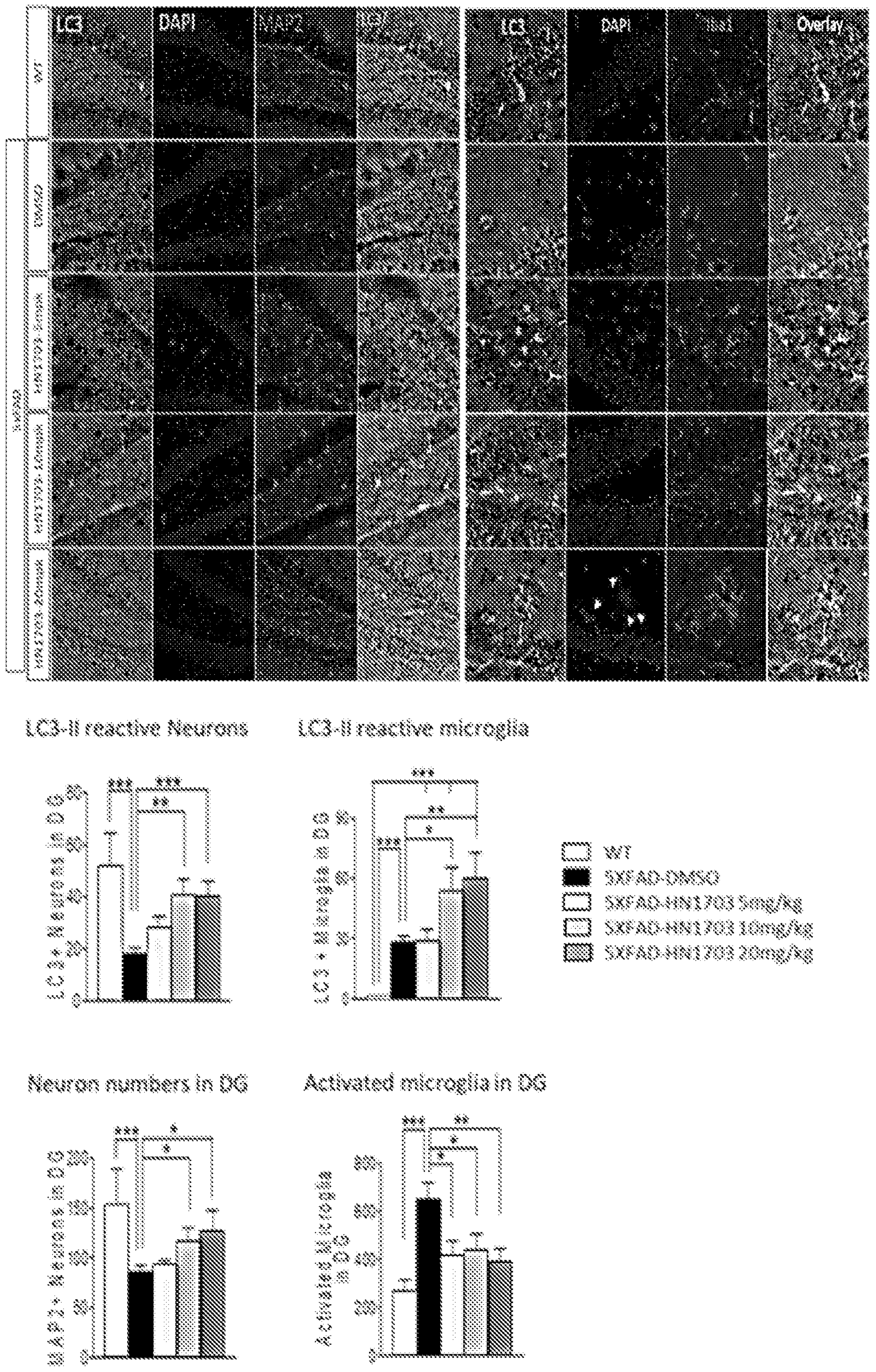
FIG. 16 illustrates confocal scanning micrographs of the hippocampal dentate gyrus region after triple staining with an Iba-1 antibody, an MAP2 antibody, and an LC3 antibody, and quantifying the number of LC3-stained neurons, the number of LC3-stained microglia, the number of MAP2-stained neurons, and the number of Iba-1-strained cells in sequence.

FIG. 16 illustrates confocal scanning micrographs of the hippocampal dentate gyrus region after triple staining with an Iba-1 antibody, an MAP2 antibody, and an LC3 antibody, and quantifying the number of LC3+/MAP2+ cells, the number of LC3+/Iba-1+ cells, the number of MAP2+ cells, and the number of Iba-1+ cells.

Referring to FIG. 16, the number of MAP2+ neurons in the dentate gyrus was greatly reduced in the 5xFAD-DMSO control group, and increased in a dose-dependent manner in the HN-1703-administered group to approach the WT normal group. The number of neurons double-stained with MAP2 and LC3-II was also significantly decreased in the 5xFAD-DMSO control group and increased in a dose-dependent manner by administration of HN-1703.

On the other hand, activated microglia, Iba-1+ cells, were increased twice or more as much in the 5xFAD-DMSO control group as compared to the WT normal group, and in the 5 to 20 mg/kg HN-1703-administered group, the Iba-1+ cells were observed more than those in the WT normal group, but all were greatly reduced compared to the 5xFAD-DMSO control group. Autophagy-activated microglia double-stained with LC3-II were rarely observed in the WT normal group, but many microglia were observed in the 5xFAD-DMSO group. In addition, as HN-1703 was administered to 5xFAD mice, the microglia were increased in a dose-dependent manner and increased twice or more as compared to the 5xFAD-DMSO control group. From these experimental results, it was confirmed that autophagy was activated in neurons and microglia in the 5xFAD dementia animal model administered with HN-1703.

Experimental Example 11. Evaluation of Neurogenesis in 5xFAD Mice

In order to evaluate an effect of HN-1703 on the neurogenesis of 5xFAD mice, brain slices were stained with an Sox2 antibody or a DCX antibody. Neural progenitor cells expressed Sox2, and differentiated neural progenitor cells expressed DCX.

Figure 17:
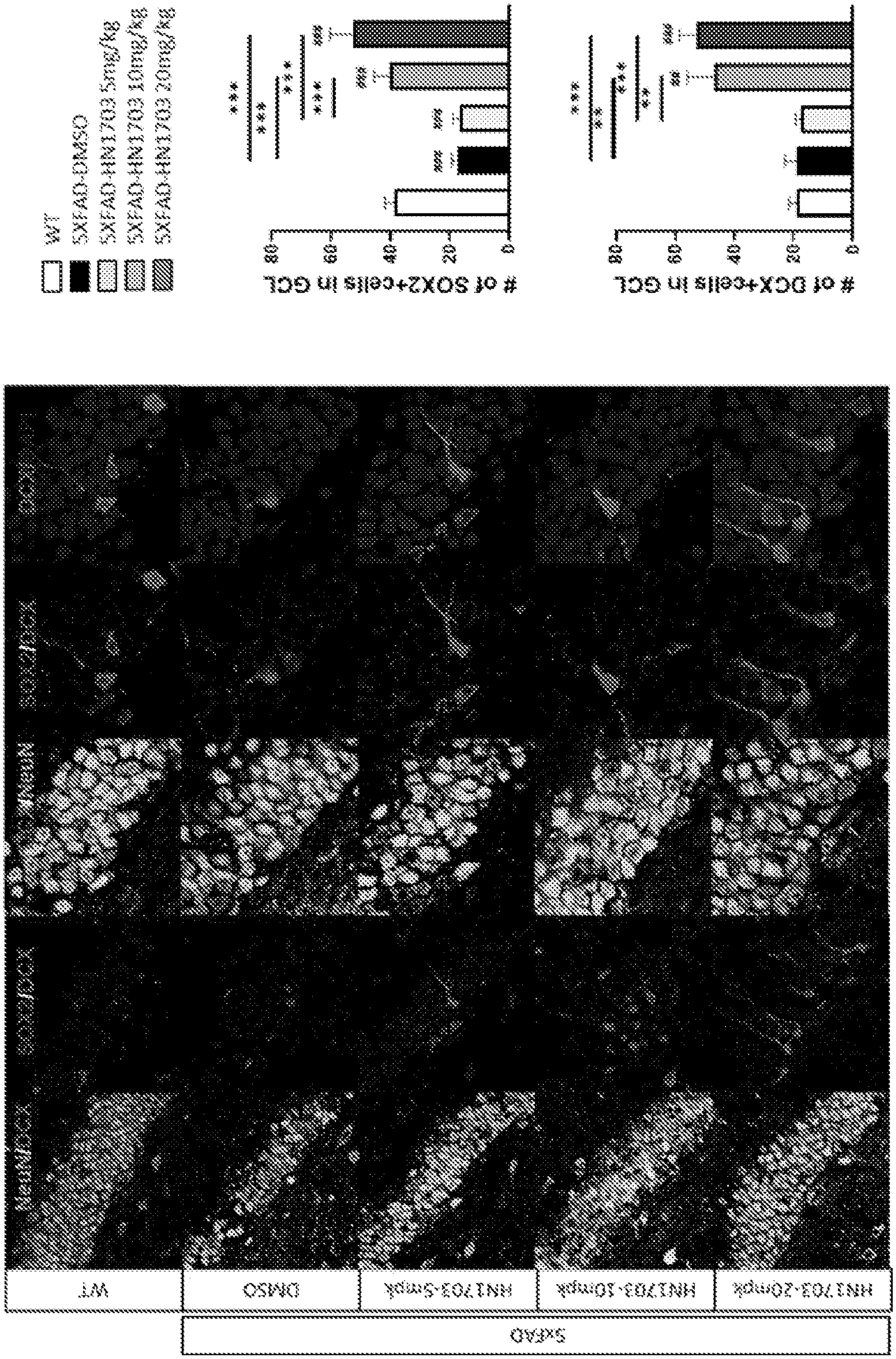
FIG. 17 illustrates confocal scanning micrographs of a subgranular zone region of the hippocampal dentate gyrus after triple staining with an NeuN antibody as a neuron marker, an Sox2 antibody as a type1 neural progenitor cell marker, and a DCX antibody as a differentiating and migrating type3 neural precursor cell marker, and quantifying the number of Sox2-stained type1 cells and the number of DCX-stained type3 cells.

FIG. 17 illustrates confocal scanning micrographs of a subgranular zone region of the hippocampal dentate gyrus after triple staining with an NeuN antibody as a neuron marker, an Sox2 antibody as a type1 neural progenitor cell marker, and a DCX antibody as a differentiating and migrating type3 neural precursor cell marker, and quantifying the number of Sox2+/NeuN+ cells and the number of DCX+/NeuN+ cells.

Referring to FIG. 17, in the 5xFAD-DMSO control group, the number of Sox2-stained neural progenitor cells was reduced by 60% or more compared to the WT normal group. In contrast, more Sox2+ neural progenitor cells were observed in the 10 to 20 mg/kg HN-1703-administered group than in the WT normal group. DCX+ neural progenitor cells that initiated cell migration and differentiation were also observed twice or more in the 10 to 20 mg/kg HN-1703-administered group as compared to the WT normal group. From these results, it was confirmed that HN-1703 promoted the division and differentiation of the neural progenitor cells in 5xFAD mice.

PREPARATION EXAMPLES OF DRUGS

The active substance according to the present invention can be formulated in various forms depending on the purpose. Hereinafter, some formulation methods of containing the active substance according to the present invention as an active ingredient will be exemplified, but the present invention is not limited thereto.

<Preparation Example 1> Preparation of Powders

| | |
|---|---|
| Active substance | 2 g |
| Lactose | 1 g |

The ingredients were mixed and then filled in an airtight bag to prepare powders.

<Preparation Example 2> Preparation of Tablets

| | |
|---|---|
| Active substance | 100 mg |
| Corn starch | 100 mg |
| Lactose | 100 mg |
| Magnesium stearate | 2 mg |

The ingredients were mixed and then tableted according to a general tablet preparing method to prepare tablets.

<Preparation Example 3> Preparation of Capsules

| | |
|---|---|
| Active substance | 100 mg |
| Corn starch | 100 mg |
| Lactose | 100 mg |
| Magnesium stearate | 2 mg |

The ingredients were mixed and then filled in gelatin capsules according to a general capsule preparing method to prepare capsules.

<Preparation Example 4> Preparation of Injections

| | |
|---|---|
| Active substance | 10 μg/ml |
| Dilute hydrochloric acid BP | Until pH 3.5 |
| Sodium chloride BP for Injection | Up to 1 ml |

The active substance of the present invention was dissolved in an appropriate volume of sodium chloride BP for injection, the pH of the generated solution was adjusted to pH 3.5 with dilute hydrochloric acid BP, and then the volume was adjusted using sodium chloride BP for injection, and mixed thoroughly. The solution was filled in a 5 ml type I ampoule made of clear glass, the glass was dissolved, and sealed under an upper grid of air, and sterilized by autoclaving at 120° C. for 15 minutes or longer to prepare injections.

<Preparation Example 5> Preparation of Nasal Sprays

| | |
|---|---|
| Active substance | 1.0 g |
| Sodium acetate | 0.3 g |
| Methylparaben | 0.1 g |
| Propylparaben | 0.02 g |
| Sodium chloride | Suitable amount |
| HCl or NaOH | Suitable amount for pH adjustment |
| Purified water | Suitable amount |

According to a conventional method for preparing nasal sprays, the nasal sprays were prepared to contain 3 mg of active substance per 1 mL of saline (0.9% NaCl, w/v, solvent was purified water), filled in an opaque spray container and sterilized.

<Preparation Example 6> Preparation of Liquids

| | |
|---|---|
| Active substance | 100 mg |
| Isomerized glucose | 10 g |
| Mannitol | 5 g |
| Purified water | Suitable amount |

According to a general method of preparing liquids, each ingredient was added and dissolved in purified water, added with lemon flavor, and then the ingredients were mixed, added with purified water to be adjusted to total 100 mL, and then filled in a brown bottle and sterilized to prepare liquids.

Hereinabove, the present invention has been described with reference to preferred embodiments thereof. It will be understood to those skilled in the art that the present invention may be implemented as a modified form without departing from an essential characteristic of the present invention. Therefore, the disclosed embodiments should be considered in an illustrative viewpoint rather than a restrictive viewpoint. The scope of the present invention is defined by the appended claims rather than by the foregoing description, and all differences within the scope of equivalents thereof should be construed as being included in the present invention.

The invention claimed is:

1. A method for treating neurodegenerative disease, comprising administering a composition comprising 7,9-dimethoxy-10H-[1,3]dioxolo[4,5-b]xanthen-10-one, or a pharmaceutically acceptable salt thereof as an active ingredient to a subject in need thereof.

2. The method of claim 1, wherein the neurodegenerative disease is at least one selected from the group consisting of dementia, Parkinson's disease, Alzheimer's disease, Pick's disease, Huntington's disease, epilepsy, stroke, apoplexy, ischemic brain disease, and memory loss.

3. The method of claim 1, wherein the neurodegenerative disease is Alzheimer's disease.

4. A method for treating mTORopathy, comprising administering the composition according to claim 1 or a pharmaceutically acceptable salt thereof as an active ingredient to a subject in need thereof.

5. The method of claim 4, wherein the mTORopathy is at least one selected from the group consisting of epilepsy, autism spectrum disorder (ASD), macrocephaly, tuberous sclerosis complex (TSC), seizure, fragile X syndrome, or intellectual disability.

6. A method for promoting neurogenesis in nervous system disease, comprising administering the composition according to claim 1 or a pharmaceutically acceptable salt thereof of as an active ingredient to a subject in need thereof.

7. The method of claim 6, wherein the promoting neurogenesis is promoting division, differentiation, migration or survival of neural stem cells or neural progenitor cells.

8. The method of claim 7, wherein the nervous system disease is at least one selected from the group consisting of traumatic central nervous system disease, spinal cord injury disease, peripheral nerve injury, amyotrophic axonal sclerosis, and peripheral nerve disease.

9. A method for inhibiting activity of mammalian target of rapamycin complex 1 (mTORC1) or mammalian target of rapamycin complex 2 (mTORC2), comprising administering the composition according to claim 1 or a pharmaceutically acceptable salt thereof of as an active ingredient to a subject in need thereof.

* * * * *